US005661033A

United States Patent [19]
Ho et al.

[11] Patent Number: 5,661,033
[45] Date of Patent: Aug. 26, 1997

[54] GENE TRANSFER USING HERPES VIRUS VECTORS AS A TOOL FOR NEUROPROTECTION

[75] Inventors: Dora Yuk-wai Ho, Mountain View; Robert Morris Sapolsky, San Francisco; Edward S. Mocarski, Jr., Menlo Park, all of Calif.

[73] Assignee: The Board of Trustees of the Leland Stanford Junior University, Stanford, Calif.

[21] Appl. No.: 287,042

[22] Filed: Aug. 8, 1994

Related U.S. Application Data

[63] Continuation-in-part of Ser. No. 981,863, Nov. 25, 1992, abandoned.

[51] Int. Cl.$^6$ .............................. C12N 15/86; C12N 7/01
[52] U.S. Cl. ................................. 435/320.1; 435/235.1
[58] Field of Search ......................... 435/69.1, 172.1, 435/172.3, 320.1; 935/23, 32, 55, 57, 62

[56] References Cited

PUBLICATIONS

Schurr et al. (1987) Brain Res 421:135–139.
Sapolsky and Stein (1989) Neurosci Lett 97:157–162.
Asano et al. (1991) Cancer Res 51:4450–4454.
Harrison et al. (1990) J Biol Chem 265:20106–20116.
Freese et al. (1990) Biochem Pharmacol 40:2189–2199.
Ho, D. Y., et al., "Altering central nervous system physiology with a defective herpes simplex virus vector expressing the glucose transporter gene," *Proc. Natl. Acad. Sci. USA* 99: 3655–3659 (1993).
Boado, R.J., and W.M. Pardridge, "Glucose Deprivation Causes Posttranscriptional Enhancement of Brain Capillary Endothelial Glucose Transporter Gene Expression via GLUT1 mRNA Stabilization," *Journal of Neurochemistry* 60(6): 2290–2296 (1993).
Boast, C.A., et al., "The N–methyl–D–aspartate antagonists CGS 19755 and CPP reduce ischemic brain damage in gerbils," *Brain Research* 442: 345–348 (1988).
Chiocca, E.A., et al., "Transfer and Expression of the lacZ Gene in Rat Brain Neurons Mediated by Herpes Simplex Virus Mutants," *The New Biologist* 2(8): 739–746 (1990).
Cox, J.A., et al., "Excitatory amino acid neurotoxicity at the N–methyl–D–aspartate receptor in cultured neurons: role of the voltage–dependent magnesium block," *Brain Research* 499: 267–272 (1989).
Dobson, A.T., et al., "A Latent, Nonpathogenic HSV–1–Derived Vector Stably Expresses β–Galactosidase in Mouse Neurons," *Neuron* 5: 353–360 (1990).
Federoff, H.J., et al., "Expression of nerve growth factor in vivo from a defective herpes simplex virus 1 vector prevents effects of axotomy on sympathetic ganglia," *Proc. Natl. Acad. Sci. USA* 89: 1636–1640 (1992).
Freese, A., et al., "HSV–1 Vector Mediated Neuronal Gene Delivery," *Biochemical Pharmacology* 40(10): 2189–2199 (1990).

Geller, A.I., et al., "Long–term increases in neurotransmitter release from neuronal cells expressing a constitutively active adenylate cyclase from a herpes simplex virus type 1 vector," *Proc. Natl. Acad. Sci. USA* 90: 7603–7607 (1993).
Geller, A.I., and X.O. Breakefield, "A Defective HSV–1 Vector Expresses *Escherichia coli* β–Galactosidase in Cultured Peripheral Neurons," *Science* 241: 1667–1669 (1988).
Gill, R., et al., "MK–801 Is Neuroprotective in Gerbils When Administered During the Post–Ischaemic Period," *Neuroscience* 25(3): 847–855 (1988).
Kaplitt, M.G., et al., "Expression of a Functional Foreign Gene in Adult Mammalian Brain following in Vivo Transfer via a Herpes Simplex Virus Type 1 Defective Viral Vector," *Molecular and Cellular Neurosciences* 2: 320–330 (1991).
Kwong, A.D., and N. Frenkel, "The Herpes Simplex Virus Amplicon IV. Efficient Expression of a Chimeric Chicken Ovalbumin Gene Amplified within Defective Virus Genomes," *Virology* 142: 421–425 (1985).
Kwong, A.D., and N. Frenkel, "Herpes Simplex Virus Amplicon: Effect of Size on Replication of Constructed Defective Genomes Containing Eucaryotic DNA Sequences," *Journal of Virology* 51(3): 595–603 (1984).
Lee, W–H., and C.A. Bondy, "Ischemic Injury Induces Brain Glucose Transporter Gene Expression," *Endocrinology* 133(6): 2540–2544 (1993).
Lysko, P.G., et al., "Excitatory amino acid neurotoxicity at the N–methyl–D–aspartate receptor in cultured neurons: pharmacological characterization," *Brain Research* 499: 258–266 (1989).
Mann, G.V., and P. Newton, "The Membrane Transport of Ascorbic Acid," *Ann. New York Acad. Sci.* 258: 243–252 (1975).
Novelli, A., et al., "Glutamate becomes neurotoxic via the N–methyl–D–aspartate receptor when intracellular energy levels are reduced," *Brain Research* 451: 205–212 (1988).
Sapolsky, R.M., et al., "Glucocorticoid toxicity in the hippocampus: in vitro demonstration," *Brain Research* 453: 367–371 (1988).

(List continued on next page.)

*Primary Examiner*—Mindy Fleisher
*Assistant Examiner*—Robert Schwartzman
*Attorney, Agent, or Firm*—Charles K. Sholtz; Peter J. Dehlinger

[57] ABSTRACT

Defective herpes simplex virus (HSV) vectors have been used to express a glucose transporter gene. The vectors were propagated using HSV conditional mutants. The efficacy of this system in vivo was tested by microinjection of the vector into adult rat hippocampus and measurement with [$^{14}$C]2-deoxyglucose uptake autoradiography, as well as measurement of kainic acid-(KA–) induced lesions. The vector significantly enhanced glucose transport and decreased neuronal damage in regions near the site of injection without causing adverse cytopathology. Neuroprotection was conferred by injecting the vector prior to, concurrently with, and following neuronal insult.

12 Claims, 18 Drawing Sheets
(1 of 18 Sheet(s) in Color)

PUBLICATIONS

Simpson, J.R., and O. Isacson, "Mitochondrial Impairment Reduces the Threshold for in Vivo NMDA–Mediated Neuronal Death in the Striatum," *Experimental Neurology* 121: 57–64 (1993).

Spaete, R.R., and N. Frenkel, "The Herpes Simplex Virus Amplicon: A New Eucaryotic Defective–Virus Clone—Amplifying Vector," *Cell* 30: 295–304 (1982).

Washko, P., and M. Levine, "Inhibition of Ascorbic Acid Transport in Human Neutrophils by Glucose," *The Journal of Biological Chemistry* 267(33): 23568–23574 (1992).

Zeevalk, G.D., and W.J. Nicklas, "Mechanisms Underlying Initiation of Excitotoxicity Associated with Metabolic Inhibition," *The Journal of Pharmacology and Experimental Therapeutics* 257: 870–878 (1991).

GENE TRANSFER USING HERPES VIRUS VECTORS AS A TOOL FOR NEUROPROTECTION

This application is a continuation-in-part of U.S. patent application Ser. No. 07/981,863, filed Nov. 25, 1992, abandoned.

FIELD OF INVENTION

The present invention relates in general to methods of reducing neuronal damage following neurological insults such as stroke, epileptic seizures, brain trauma, hypoglycemia and neurodegenerative diseases. The invention relates more specifically to herpes-virus-based vectors that make neurons resistant to excitotoxic insults.

REFERENCES

Albin, R., et al., *New Eng. J. Med.* 322:1293 (1990).

Asano, T., et al., *Biophys. Res. Commun.* 154:1204–1211 (1988).

Asano, T., et al., *Nucleic Acids Res.* 17:6386 (1989).

Ausubel, F. M., et al., *Current Protocols in Molecular Biology*, John Wiley and Sons, Inc., Media Pa.

Auer, R., et al., *Ann. Neurol.* 24:699–714 (1988).

Barbour, B., et al., *Nature* 335:433 (1988).

Beal, M:, et al., *Brain Res.* 361:135 (1985).

Beal, M., et al., *Nature* 321:168 (1986).

Beal, M., *Ann. Neurol.* 31:119 (1992).

Ben-Ari, Y., *Neuroscience* 14:375 (1985).

Birnbaum, M. J., et al., *Proc. Natl. Acad. Sci. U.S.A.* 83:5784–5788 (1986).

Birnbaum, M. J., *Cell* 57:305–15 (1989).

Blaustein, M., *Trends Neurosci.* 11:438 (1988).

Boast, C. A., et al., *Brain Res.* 442:345 (1988).

Boast, C. A., et al., *Excitatory Amino Acid Transmission* (T. Hicks, et al., Eds.) (Alan R. Liss, New York, N.Y.) pp. 249–152 (1987).

Boast, C. A., et al., *Brain Res.* 265:157 (1983).

Boegman, R., et al., *Brain Res.* 415:178 (1987).

Chan, P., et al., *Ann. Neurol.* 29:482 (1991).

Charron, M. J., et al., *Proc. Natl. Acad. Sci. U.S.A.* 86:2535–2539 (1989).

Cherrington, J. M., et al., *J. Virol.* 63:1435–1440 (1989).

Cheung, J., et al., *New. Eng. J. Med.* 26:1670 (1986).

Chiocca, E. A., et al., *New. Biol.* 2:739–746 (1990).

Choi, D., *Neurosci. Lett.* 58:293 (1985).

Choi, D., *J. Neurosci.* 7:357 (1987).

Choi, D., *Neuron* 1:623 (1988a).

Choi, D., *Trends Neurosci.* 11:465 (1988b).

Coyle, J., et al., *Nature* 263:244 (1976).

Coyle, J., and Puttfarcken, P., *Science* 262:689 (1993).

Cushman, S., et al., *J. Biol. Chem.* 255:4758 (1980).

Dagani, F., et al., *J. Neurochem.* 49:1229 (1987).

Davies, S., et al., *Neuroscience* 26:387 (1988).

DeLuca, N., et al., *J. Virol.* 56:558 (1985).

Dobson, A. T., et al., *Neuron* 5:353–360 (1990).

Dormitzer, P. R., et al., *Virology* 187:18–32 (1992).

Drejer, J., et al., *J. Neurochem.* 34:145 (1985).

Dutch, R. E., et al., *J. Virol.* 66:277–285 (1992).

Elias, P., et al., *Proc. Natl. Acad. Sci. U.S.A.* 83:6322–6326 (1986).

Elliot, E., et al., *Soc. Neurosci. Abst.* 16:78.8 (1990).

Elliot, E., et al., *J. Neurochem.* 59:1033 (1992).

Frenkel, N., *Human Herpesviruses—An Interdisciplinary Prospective*, New York: Elsevier/North-Holland (1981).

Fukumoto, H., et al., *Proc. Natl. Acad. Sci. U.S.A.* 85:5434–5438 (1988).

Fukumoto, H., et al., *J. Biol. Chem.* 264:7776–7779 (1989).

Garvey, W., et al., *Mol. Endocrinol.* 47:1132–1139 (1989).

Geller, A. I., et al., *Science* 241:1667–1669 (1988).

Geller, A. I., et al., *Proc. Natl. Acad. Sci. U.S.A.* 87:1149–1153 (1990).

Gill, R., et al., *Neuroscience* 25:847 (1988).

Goldberg, R., et al., *N. Neurosci.* 6:3144 (1986).

Greenamyre, et al., *Neurobio. Aging* 10:593 (1989).

Halpain, S., et al., *Neuroendocrinology* 48:235 (1988).

Harlow, E., et al., *Antibodies: A Laboratory Manual*, Cold Spring Harbor Laboratory Press (1988).

Haspel, H. C., et al., *J. Biol. Chem.* 260:7219–7225 (1985).

Haspel, H. C., et al., *J. Biol. Chem.* 263:398–403 (1988).

Hawley-Nelson, P., et al., *Focus* 15:3 (1993).

Ho, D. Y., et al., *Virology* 167:279–283 (1988).

Ho, D. Y., et al. *Proc. Natl. Acad. Sci. U.S.A.* 86:7596–7600 (1989).

Hockenbery, D. M., et al., *Cell* 75:2241–251 (1993).

Horner, H. C., et al., *J. Bio. Chem.* 262:17696–17702 (1987).

Horner, H. C., et al., *Neuroendocrinology* 52:57–64 (1990).

Hughes, R. G., et al., *J. Virol.* 16:275–283 (1975).

Hunziker, W., and Schrickel, S., *Mol. Endocrin.* 2:465–473 (1988).

James, D. E., et al., *Nature* 338:83–87 (1989).

Jang, S. K., et al., *J. Virol.* 8:2636–2643 (1988).

Johansen, F., et al., *Acta Neuropathol.* 71:46 (1988).

Kadekaro, M., et al., *Neuroendocrinology* 47:329–336 (1988).

Kaestner, H. K., et al., *Proc. Natl. Acad. Sci. U.S.A.* 85:5434–5438 (1988).

Kaplitt, M. G., et al., *Mol. Cell. Neurosci.* 2:320–330 (1991).

Kayano, T., et al., *J. Biol. Chem.* 263:15245–15248 (1988).

Kohler, C., et al., *Brain Res.* 211:485 (1981).

Kowall, N., et al., *Trends Neurosci.* 10:24 (1987).

Kwong, A. D., et al., *Virology* 142:421–425 (1985).

Kwong, A. D., et al., *J. Virol.* 63:4834 (1989).

Levy, D. I., and Lipton, S. A., *Neurology* 40:852 (1990).

Lieman-Hurwitz, J., et al., *Proc. Natl. Acad. Sci. U.S.A.* 79:2808–2811 (1982).

Maniatis, T., et al., *Molecular Cloning: A Laboratory Manual*, Cold Spring Harbor Laboratory (1982).

Manning, W. C., et al., *Virology.* 167:477–484 (1988).

Marsh, J. L., *Gene* 32:481–485 (1984).

McConnell, H. M., *Science* 257:1906 (1992).

McGeer, E., et al., *Nature* 263:517 (1976).

McGeoch, D. J., et al., *Nuc. Acids Res.* 14:1727–1745 (1986).

Meldrum, B., *Adv. Neurol.* 34:261 (1983).

Mueckler, M., et al., *Science* 29:941–945 (1985).

Munck, A., *Perspect. Biol Med* 14:265–284 (1971).

Novelli, A., et al., *Brain Res.* 453:367 (1988).

Pardridge, W. M., et al., *J. Bio. Chem.* 265:18035–18040 (1991).

Raley-Susman, K. M., et al., *J. Neurosci.* 12:773 (1992).

Roberts, R., et al., *J. Comp. Neurol.* 274:406 (1988).

Roizman, B., et al., *Virology*, 2nd Edition (Fields, B., et al., eds.) Raven Press, NY (1990).

Rosen, D. R., et al., *Nature* 362:59–62 (1993).

Rosen-Wolff, A., et al., *Virus Genes.* 4:325–337 (1990).

Sapolsky, R., *J. Neurosci.* 6:2240–2247 (1986).

Sapolsky, R., et al., *Brain Research* 453:367 (1988).

Sapolsky, R., et al., *Neurosci. Letts.* 97:157 (1989).

Sapolsky, R., *Prog. Brain Research* 86:13–23 (1990).

Sambrook, J., et al., In *Molecular Cloning: A Laboratory Manual*, Cold Spring Harbor Laboratory Press, Vol. 2 (1989).

Scharfman, H., et al., *Science* 246:257 (1989).

Schurr, A., et al., *Brain Res.* 421:135 (1987).

Seisjo, B., *Brain Energe Metabolism*, Wiley, New York (1978).

Siesjo, B. J., *Cerebral Blood Flow Metabolism*. 1:155–173 (1981).

Shih, M. F., et al., *Proc. Natl. Acad. Sci. U.S.A.* 81:5867–5870 (1984).

Siman, R., et al., *Neuron* 1:279 (1988).

Spaete, R. R., et al., *Cell* 30:295–304 (1982).

Stein, B., et al., *Brain Res.* 473:175 (1988).

Sutin, E. L. and Kilduff, T. S., *Mol. Brain. Res.* 15:281–290 (1992).

Thorens, B., et al., *Cell* 55:281–290 (1988).

Tombaugh, G., et al., *Cereb. Blood Flow Metab.* 10:527 (1990).

Varmuza, S. L., et al., *Cell* 41:793–802 (1985).

Vaux, D. L., et al., *Nature* 335:440–442 (1988).

Vibulsreth, S., et al., *Science* 241:981 (1988).

Virgin C., et al., *J. Neurochem.* 57:1422–1428 (1991).

Weiler-Gluttler, H., et al., *Biol. Chem. Hoppe-Seyler* 340:467–473 (1989).

Welch, W., *Physiological Rev.* 72:1063 (1992).

Young, A., et al., *Science* 241:981 (1988).

Yu, A. C. H., et al., *J. Neurochem.* 42:951–960 (1984).

Zar, J., *Biostatistical Analysis*, 2nd Edition (Prentice-Hall, Englewood Cliffs, N.J.) (1984).

Zhong, L.-T., et al., *Proc. Natl. Acad. Sci. U.S.A.* 90:4533–4537 (1993).

BACKGROUND OF THE INVENTION

Progress has been made in recent years in linking selective neuron loss during various neurological disorders to the actions of excitatory amino acid (EAA) neurotransmitters. EAAs such as glutamate and aspartate are bound by a family of receptors; of these, it is the NMDA receptor which is most implicated as a mediator of neurotoxicity.

In hypoxia-ischemia, hypoglycemia, seizure and brain trauma, there is excessive extracellular accumulation of EAAs in vulnerable brain regions. Moreover, N-methyl-D-aspartate (NMDA) receptor blockade protects against these insults (Choi, 1988a). Similarly, a dominant theory regarding the pathogenesis of Huntington's Disease (HD) focuses on excessive exposure to EAAs. As evidence, there is preferential loss of NMDA-receptor bearing neurons in both symptomatic and pre-symptomatic cases (Young et al.; Albin et al.). Moreover, striatal lesions induced by EAA analogs reproduce many of the neuropathologic and neurochemical features of HD (Coyle et al.; McGeer et al.; Beal et al., 1985, 1986; Davies et al.; Roberts et al.; Boegman et al.; Kowall et al.). Some investigators have even suggested that the degeneration typical of Alzheimer's Disease (AD) might be mediated by EAAs (Greenamyre et al.).

One theme common to excitotoxic insults is that they constitute crises of energy. EAA exposure (in animal models of HD) and seizure represent pathologic increases in energy demands, while hypoxia-ischemia and hypoglycemia represent pathologic disruptions of substrate delivery. In all cases, there are declines in ATP and phosphocreatine concentrations (Auer et al.).

Glucose supplementation has been shown to protect neurons from these insults. In cases of hypoglycemia glucose supplementation mitigates the primary insult: in hypoxia-ischemia, this can be shown using cell number or function as an endpoint (Goldberg et al.; Tombaugh et al.; Schurr et al.). For seizure, increased glucose availability at the time of insult attenuates damage (Meldrum; Johansen et al.; Sapolsky et al., 1989). Finally, energy depletion shifts EAAs from being neurotransmitters to being neurotoxins (Novelli et al.).

The energetic nature of these insults may be a consequence of the mechanisms of EAA and calcium trafficking. Energy depletion enhances both calcium-dependent and independent glutamate release (Drejer et al.; Dagani et al.). Furthermore, energy failure impairs high-affinity glutamate re-uptake into neurons (Drejer et al.), which enhances glutamate neurotoxicity (Kohler, et al.; Choi, 1987). Glutamate uptake into glia is also energy-dependent (Barbour et al.), and diminution of the glial component of glutamate uptake also enhances toxicity (Vibulsreth et al.).

The calcium component of neurotoxicity is also augmented by energy failure. In all of the above-described scenarios of neuron death, one consequence of the EAA excess is mobilization of free cytosolic calcium in the post-synaptic neuron. This mobilization arises from opening of a calcium channel gated to the NMDA-receptor (whose regulation is vastly complex), opening of voltage-gated calcium channels, and mobilization of calcium from intracellular stores by sodium and inositol phosphate second messengers (Choi, 1988b; Blaustein). Critically, prevention of such a rise (for example, by removal of calcium from culture media, or microinjection of calcium chelators into neurons) is neuroprotective (Choi, 1985; Goldberg et al.; Scharfman et al.).

Excessive free cytosolic calcium, in turn, is thought to be cytotoxic by indiscriminately activating various calcium-dependent proteases, lipases and nucleases, leading to free radical formation, membrane damage, DNA fragmentation, and so on (Cheung et al.). In neurons, probably the best-studied of degenerative consequences of calcium excess is the proteolysis of various cytoskeletal proteins (Siman et al.).

Experiments performed in support of the present invention support a method to buffer neurons from EAA toxicity. A herpes virus vector is used to deliver a glucose transporter (GT) gene into neurons, in order to cause overexpression and increase glucose transport into infected neurons. The experiments further demonstrate that expression of the GT gene is effective to reduce neuronal injury even when the vector is administered after the neurological insult.

SUMMARY OF THE INVENTION

It is one general object of the invention to provide an amplicon which includes herpes simplex virus (HSV) sequences. The amplicon typically includes bacterial plasmid sequences that allow the amplicon to be amplified in prokaryotic cells. The amplicon further contains an HSV origin of DNA replication and HSV cleavage/packaging signals, and sequences coding for genes effective to provide neuroprotection when expressed (i.e. neuroprotective genes). Neuroprotective genes include genes encoding glucose transporter protein, apoptosis-suppressor bcl-2, calbindin D28K, superoxide dismutase (SOD) and heat shock protein 72 (HSP72). The neuroprotective gene coding sequences can be obtained from a number of sources, including rat or human DNA coding sequences. In the amplicon the neuroprotective gene coding sequences are flanked by regulatory elements effective to allow expression of the coding sequences in a eucaryotic host. Typically, the regulatory elements flanking the neuroprotective gene coding sequences include a promoter, a translation start, and polyadenylation signals. These regulatory elements can be obtained from a number of sources including the human cytomegalovirus ie1 gene and the herpes simplex virus ICP4 gene.

In one embodiment of the present invention, the neuroprotective gene coding sequences are glucose transporter protein coding sequences.

In another embodiment of the present invention, the HSV sequences in the amplicon are derived from Herpes Simplex Virus I.

It is another object of the invention to provide an expression vector which contains at least one copy of the amplicon of the present invention. The expression vector includes a defective herpes virus into which at least one copy of the amplicon has integrated: usually, multiple copies of the amplicon integrate into the defective herpes virus vector.

The invention also includes, a method of making the above-described defective virus expression vector. The method includes generating an amplicon that contains the following: (i) herpes simplex virus (HSV) sequences containing an HSV origin of DNA replication and HSV cleavage/packaging signals; (ii) glucose transporter protein coding sequences, where the coding sequences are flanked by regulatory elements effective to allow expression of the coding sequences in a eucaryotic host; and (iii) bacterial plasmid sequences that allow the vector to be amplified in prokaryotic cells. The amplicon is co-transfected into a permissive eucaryotic cells with a helper virus, where the helper virus is a conditionally replication-defective herpes simplex virus. The eucaryotic cells are then passaged, to allow propagation of the viruses, and ultimately the defective virus is released from the cells.

In this method, the herpes simplex virus can be rendered conditionally replication-defective by, for example, the presence of a temperature-sensitive replication defective mutation or a deletion in a gene required for replication. In one aspect of the method of the present invention, the permissive eucaryotic cell carries a functional copy of the gene required for replication.

Also forming part of the invention is a method of protecting neuronal cells in a mammal from neurological insult. In this method, neuronal cells are infected with the above-described defective herpes virus, which contains at least one copy of the amplicon. The infection of the cells can be carried out before during or after the neurological insult.

The present invention also describes a method of increasing glucose transport into neuronal cells. In this method, neuronal cells are infected with a defective herpes virus, such as one described above, which contains at least one copy of an amplicon containing glucose transporter protein coding sequences.

Also included in the present invention is a method of reducing damage of neuronal cells, due to a neurological insult, in a mammal. This method includes infecting the neuronal cells with a defective herpes virus into which at least one copy of an amplicon has integrated, where the amplicon contains (i) herpes simplex virus (HSV) sequences containing an HSV origin of DNA replication and HSV cleavage/packaging signals, (ii) neuroprotective gene protein coding sequences, where the coding sequences are flanked by regulatory elements effective to allow expression of the coding sequences in a eucaryotic host, and (iii) bacterial plasmid sequences that allow the amplicon to be amplified in prokaryotic cells. The infecting in this method can take place before, during or after the neurological insult. The neuroprotective gene coding sequences useful in this method include coding sequences of the following proteins: glucose transporter protein, apoptosis-suppressor bcl-2, calbindin D28K, superoxide dismutase (SOD) and heat shock protein 72 (HSP72).

These and other objects and features of the invention will become more fully apparent when the following detailed description is read in conjunction with the accompanying drawings.

BRIEF DESCRIPTION OF THE FIGURES

The file of this patent contains at least one photograph executed in color. Copies of this patent with color photograph(s) will be provided by the Patent and Trademark Office upon request and payment of necessary fee.

DETAILED DESCRIPTION OF THE INVENTION

I. Construction of Amplicons and Generation of Defective Vectors.

Defective viral vectors, capable of expressing a neuroprotective gene, such as glucose transporter protein, in neuronal and glial cells, are generated in experiments performed in support of the present invention. First, an amplicon containing the coding sequence of interest is generated. Second, defective viruses carrying the coding sequence of interest are generated by co-infection of cells with the amplicon and a helper virus.

Any of a variety of genes encoding neuroprotective proteins may be used in viral vector constructs of the present invention. They include apoptosis-suppressor bcl-2 (Vaux, et al.), calbindin D28K (Hunziker and Schrickel), superoxide dismutase (SOD, Lieman-Hurwitz), heat shock protein 72 (HSP72, Welch) and glucose transporter (GT) protein (Birnbaum et al., 1986; Pardridge et al.).

Example 2 describes the generation of amplicons carrying a cDNA encoding the GLUT-1 isoform of the glucose transporter (GT) protein, initially isolated from rat brain endothelium (Birnbaum et al., 1986; Pardridge et al.). Other sources of glucose transporter protein coding sequences include human, rabbit, pig, and mouse brain (Mueckler, et al.; Birnbaum, et al., 1986, 1986; Asano, et al., 1988; Weiler-Gluttler, et al.; Kaestner, et al.; Fukumoto, et al., 1988; Thorens, et al.; Asano, et al., 1989; Kayano, et al., 1988; Fukumoto, et al., 1989; James, et al.; Birnbaum, et al., 1989; Charron, et al.; and Kayano, et al., 1990).

Figure 1A:
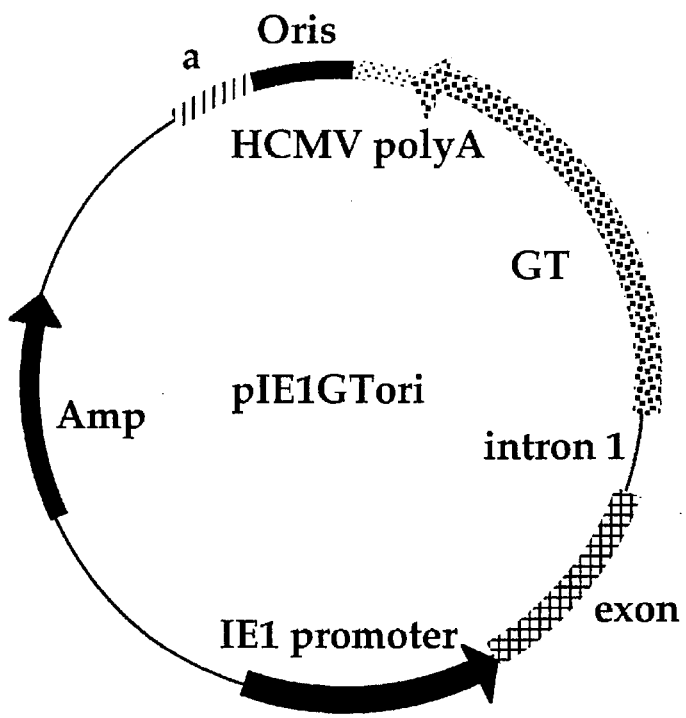
FIGS. 1A and 1B present schematic diagrams depicting the structures of pIE1GTori and pIE1βgalori, respectively. The transcriptional units of the two amplicons are driven by the HCMV ie1 promoter-enhancer. Exon 1 of ie1 is untranslated and intron 1 is spliced. The polyA signal inserted downstream of the GT gene is derived from the HCMV ie1 gene, while that of lacZ is derived from the SV40 early gene. The ori$_S$ (295 bp) and the a sequence (330 bp) are originated from HSV-1 strain F and strain KOS, respectively, and provide the necessary HSV replication signals. The ampicillin gene of the parent plasmid pGEM2 is also indicated.
Figure 1B:
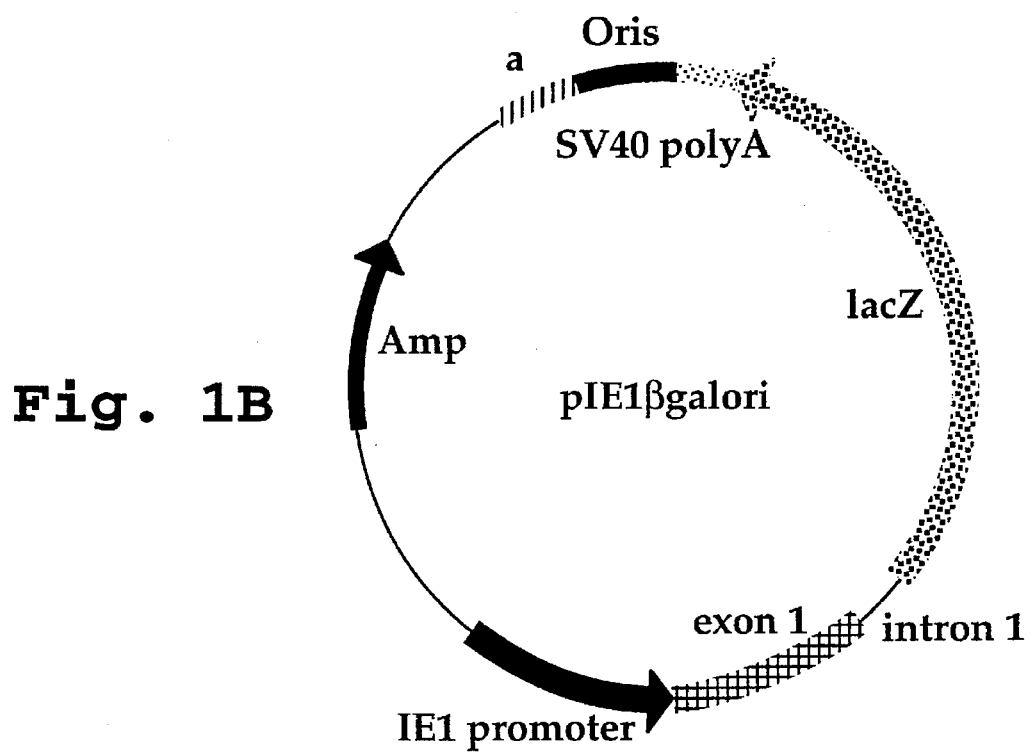

In one construct (pIE1GTori), the GT gene is put under the control of the human cytomegalovirus (HCMV) ie1 promoter-enhancer, which allows for constitutively strong expression in many different cell types, and is terminated with an HCMV ie1 polyadenylation (polyA) signal. Exon 1 is untranslated and intron 1 is spliced. This transcriptional unit is inserted in a pGEM-2 backbone with HSV ori$_s$ and a sequences included to provide necessary HSV replication and packaging signals. A corresponding control construct (pIE1βgalori) is made by replacing the GT gene with the *Escherichia coli* lacZ gene (FIG. 1B) and the HCMV ie1 polyA signal with an SV40 polyA signal. pIE1GTori and pIE1βgalori are termed IE1 amplicons and are particularly useful in cell culture (in vitro) studies of neuroprotection.

Figure 2A:
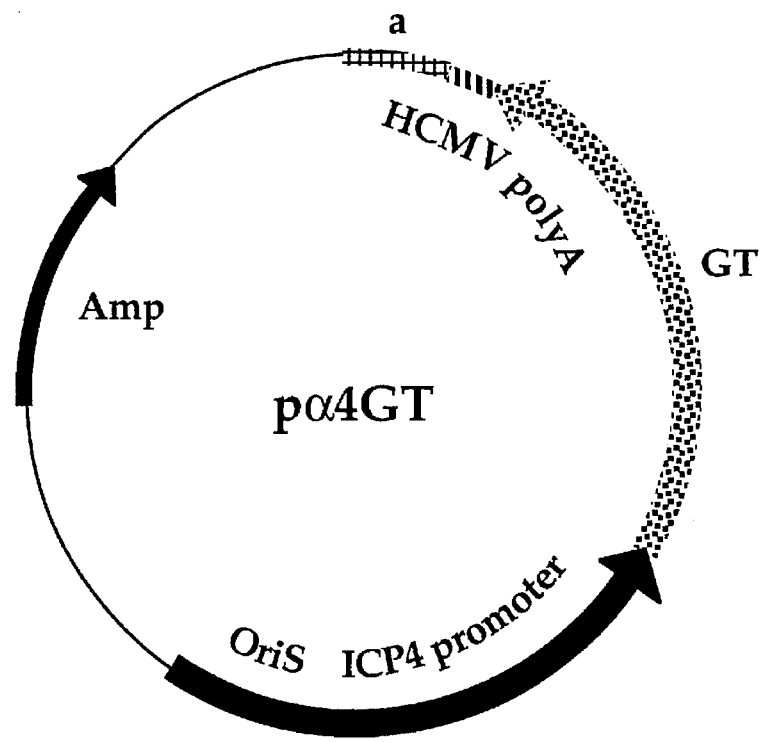
FIGS. 2A, 2B and 2C present schematic diagrams depicting the structures of pα4GT, pα4βgal and pα22βgalα4GT, respectively. The transcriptional units of pα4GT and pα4βgal are driven by the HSV-1 ICP4 (α4) promoter-enhancer. pα22βgalα4GT has two transcriptional units, one containing GT and the other lacZ. The GT unit is driven by the α4 promoter, while the lacZ unit is driven by the HSV-1 α22 promoter-enhancer. The polyA signal inserted downstream of GT gene of pα4GT and pα22βgalα4GT is derived from the HCMV ie1 gene, while the polyA signal inserted downstream of the lacZ gene of pα4βgal and pα22βgalα4GT is derived from the SV40 early gene. The remaining elements are as indicated in FIGS. 1A–C and discussed in Example 2.
Figure 2B:
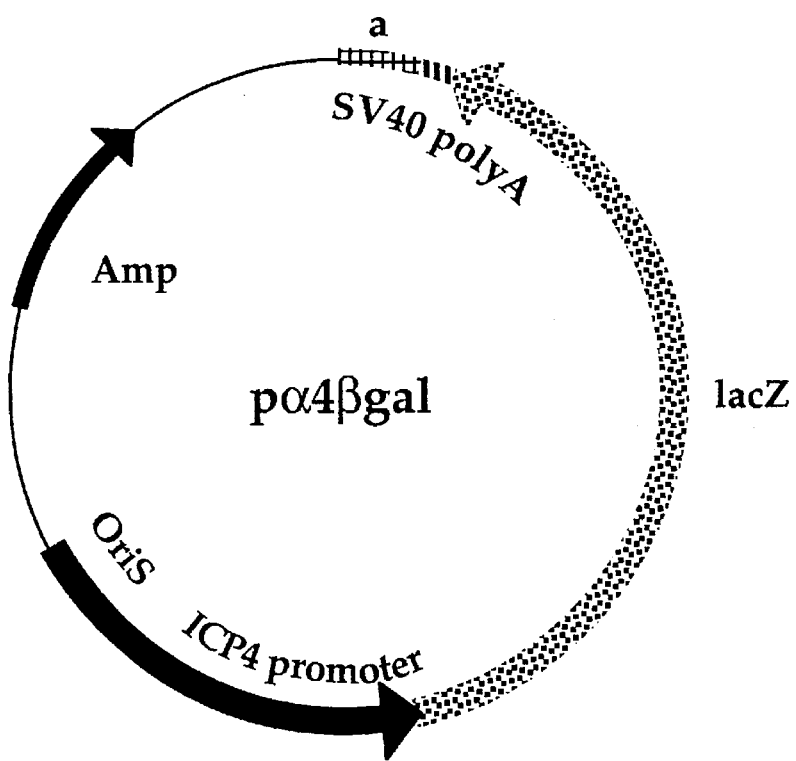

In another construct described in Example 2 (pα4GT; FIG. 2A), the GT transcriptional unit is controlled by the HSV α4 promoter and is terminated by an SV40 polyA signal. The HSV sequence which provides the α4 promoter also contains the ori$_s$. No exon or intron is present in this construct. A related control construct (pα4βgal; FIG. 2B) is synthesized by placing the lacZ gene under the control of the α4 promoter and an HCMV ie1 polyadenylation (polyA) signal. pα4GT and pα4βgal are termed α4 amplicons and are particularly useful as in vivo neuroprotection vectors.

Figure 2C:
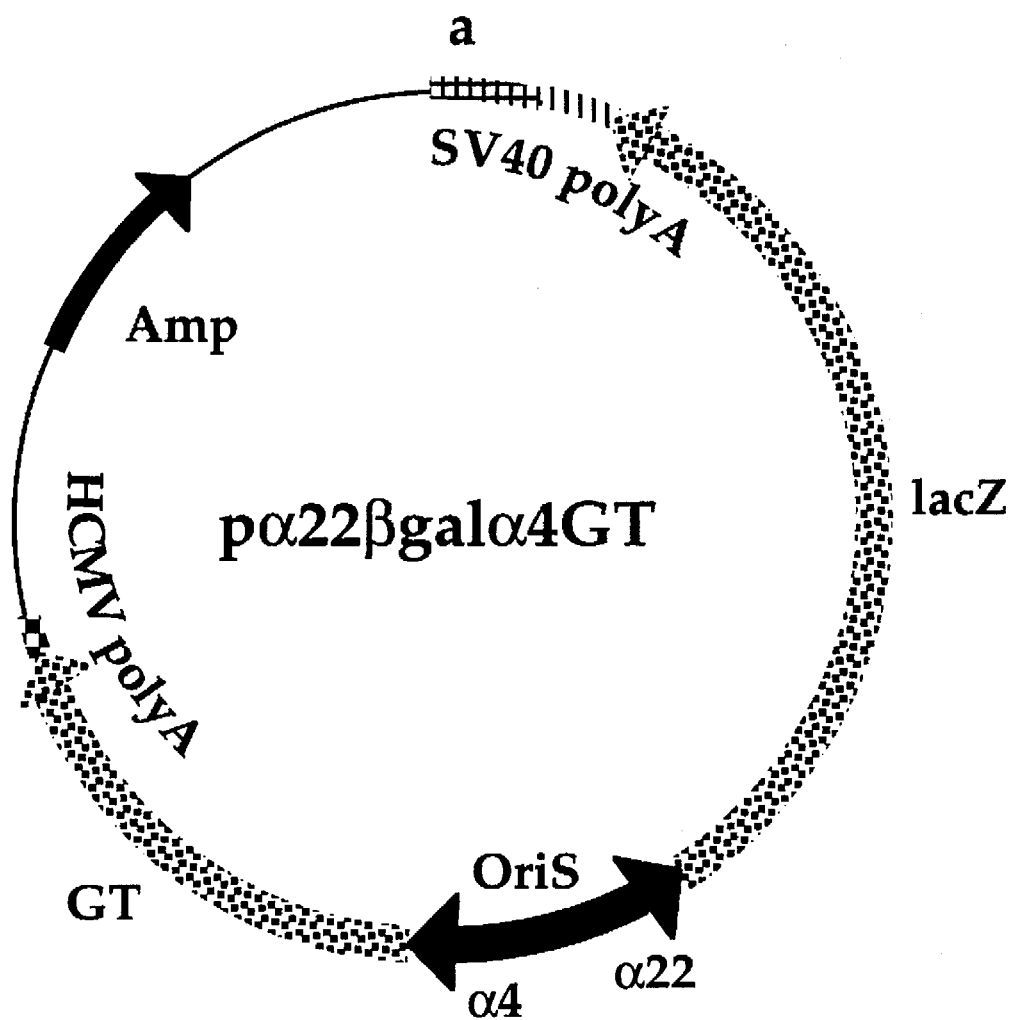

Two additional amplicons are synthesized as detailed in Example 2, and are used to generate bicistronic vectors. In pα22βgalα4GT (FIG. 2C), the GT and lacZ transcriptional units are driven by the HSV α4 and α22 immediate early promoters and terminated by HCMV polyA and SV40 polyA signals, respectively. Viral vectors generated using this amplicon expressing both GT and β-galactosidase (β-gal) at high levels. A control plasmid pα22βgalα4gts is constructed by the removal of a 450 bp BamHI fragment encompassing GT codons 23–167 and the further insertion of a linker containing termination codons. Viral vectors generated with pα22βgalα4gts express β-gal but not GT.

Defective virus vectors carrying neuroprotective gene coding sequences, such as GT coding sequences, can be generated by, for example, co-transfecting an amplicon, such as pIE1GTori or pIE1βgalori, along with genomic DNA of ts756 into Vero cells and then serially passaging the viral stocks at 33° C. using a 1:4 dilution to encourage growth of defective virus (Example 3). The virus stocks thus generated from pIE1GTori and pIE1βgalori are referred to as vIE1GT and vIE1βgal, respectively.

Alternatively, defective virus vectors can be generated by transfecting the amplicon DNA then superinfecting with the helper virus. This approach is described for amplicons pα4GT and pα4βgal (Example 3), which are used to generate virus stocks vα4GT and vα4βgal, respectively. Virus stocks vα22βgalα4GT and vα22βgalα4gts are similarly generated using amplicons pα22βgalα4GT and pα22βgalα4gts, respectively.

The development of HSV vectors of the present invention capitalizes on the natural occurrence of defective interfering particles, which arise during high multiplicity propagation of HSV (Frenkel). These defective DNA molecules are the same size as standard virus (152 kbp) but consist of head-to-tail concatemers of small regions of the viral genome including an origin of DNA replication (ori$_S$ or ori$_L$) and a cleavage/packaging signal (a sequence). Typically, the defective viruses replicate and package in the presence of a replication competent helper virus. Cloning-amplifying vectors (termed amplicons), consisting of a procaryotic plasmid for amplification in bacterial host along with the important cis-acting HSV regulatory sequences for propagation in eucaryotic cells, have been constructed based on these observations (Spaete et al.).

Studies performed in support of the present invention utilize the HCMV ie1 promoter-enhancer and a ts mutant of HSV-1 as a helper virus, or the HSV-1 α4 promoter-enhancer and a deletion mutant of HSV-1, d120, as a helper virus (DeLuca, et al., 1985). Other amplicon/helper virus systems, including other HSV-1 and HSV-2 variants, may be used to generate defective viral vectors, capable of expressing a glucose transporter protein in neuronal and glial cells, following the guidance presented herein.

Another promoter useful in the practice of the present invention is the latency-associated transcripts (LAT) promoter from HSV-1, which can cause long-termed gene expression in latently infected animals (Hoet al, 1989). Thus, the LAT promoter and other promoters from housekeeping genes may be effective to cause sustained changes in CNS function. Furthermore, two or more transcriptional units can be put on the vector by using multiple promoters or signal sequences that allow bicistronic transcription (Jang, et al.).

The neuroprotective gene protein coding sequences are typically flanked by regulatory elements effective to allow expression of the coding sequences in a eucaryotic host. Such regulatory elements include 5' transcription promoter sequences, transcription enhancer sequences, translation start signals (usually an in-frame ATG or in-frame fusion to the N-terminal coding sequences of another protein), and transcription termination sequences, including at least one 3' polyadenylation signal.

One example of a helper virus is the herpes simplex virus type 1 (HSV-1) temperature sensitive mutant, ts756 (Hughes, et al.) ts756 has a mutation in ICP4, an essential regulatory α gene of the virus and is completely replication defective at 39° C. ICP4 is an immediate early protein of HSV-1. It is responsible for the activation of most of other HSV-1 genes and is essential for viral replication (reviewed in Roizman, et al.). With respect to the helper virus, the internal body temperature of the rat is not completely non-permissive for ts756 replication so the cytopathic effects from this virus were examined. With the exception of mild gliosis around the injection site, neither the present experiments nor those conducted by others (Kaplitt et al.) have observed significant cytopathology from such defective HSV vectors.

Viruses carrying deletion mutations (Geller, et al., 1990) in key regulatory genes such as ICP4 and ICP0 may also be employed as helper viruses useful in the method of the present invention. Such as the alternative helper virus dl120, a deletion mutant which is deficient in ICP4 (DeLuca et al.). When this helper virus is used, the virus stock can be passaged in E5, a cell line which expresses ICP4 and can complement the growth of dl120.

One method to optimize the production of a neuroprotective protein, such as glucose transporter protein, in infected cells is as follows. A virion component, termed the virion host shutoff function (vhs), is responsible for shutting off host mRNA translation after HSV-1 infection (Kwong et al., 1989). To maximize the production of the neuroprotective protein in infected cells a new recombinant mutant helper virus, which is deficient in both ICP4 and vhs, can be used.

II. Characterizations Following the Introduction of Glucose Transporter Protein Coding Sequences Into Cells.

A number of techniques can be used to evaluate the expression of neuroprotective gene sequences, such as glucose transporter coding sequences, in infected cells. RNA blotting techniques (Ausubel, et al.; Maniatis, et al.) are used to measure the level of transcription of the neuroprotective gene. Western blotting (Ausubel, et al.; Harlow, et al.) and immunoprecipitation (Harlow, et al.) techniques are employed to look at the level and post-translational processing of the protein. Expression of the neuroprotective protein in infected cells can also be detected in situ by immunofluorescence. Moreover, functional assays specific for a particular neuroprotective gene may be used. For example, the functional expression of the glucose transporter can be assayed by the 2-deoxyglucose uptake and the number of glucose transporter present can be quantitated by the cytochalasin B binding method (see below).

A. Immunoprecipitation of GT from Cells Infected with a Vector Carrying GT Coding Sequences.

One method employed to confirm enhanced GT expression in infected cells is immunoprecipitation (Example 4). Vero cells are mock-infected or infected with defective vectors with (FIG. 3, lane 2) or without (FIG. 3, lanes 1, 3 and 4) the treatment of tunicamycin and are labelled with [$^{35}$S]-methionine from 13 to 16 hr post infection. Membrane fractions are then prepared and immunoprecipitated with an anti-GT rabbit serum. The immune complexes are subjected to SDS-PAGE (12% gel) and visualized by autoradiography. In the autoradiogram shown in FIG. 3: Lane 1, infected with vIE1βgal; lanes 2 and 3, infected with vIE1GT; lane 4, mock-infected. The sizes of protein standards are shown on the left.

Figures 3, 5:
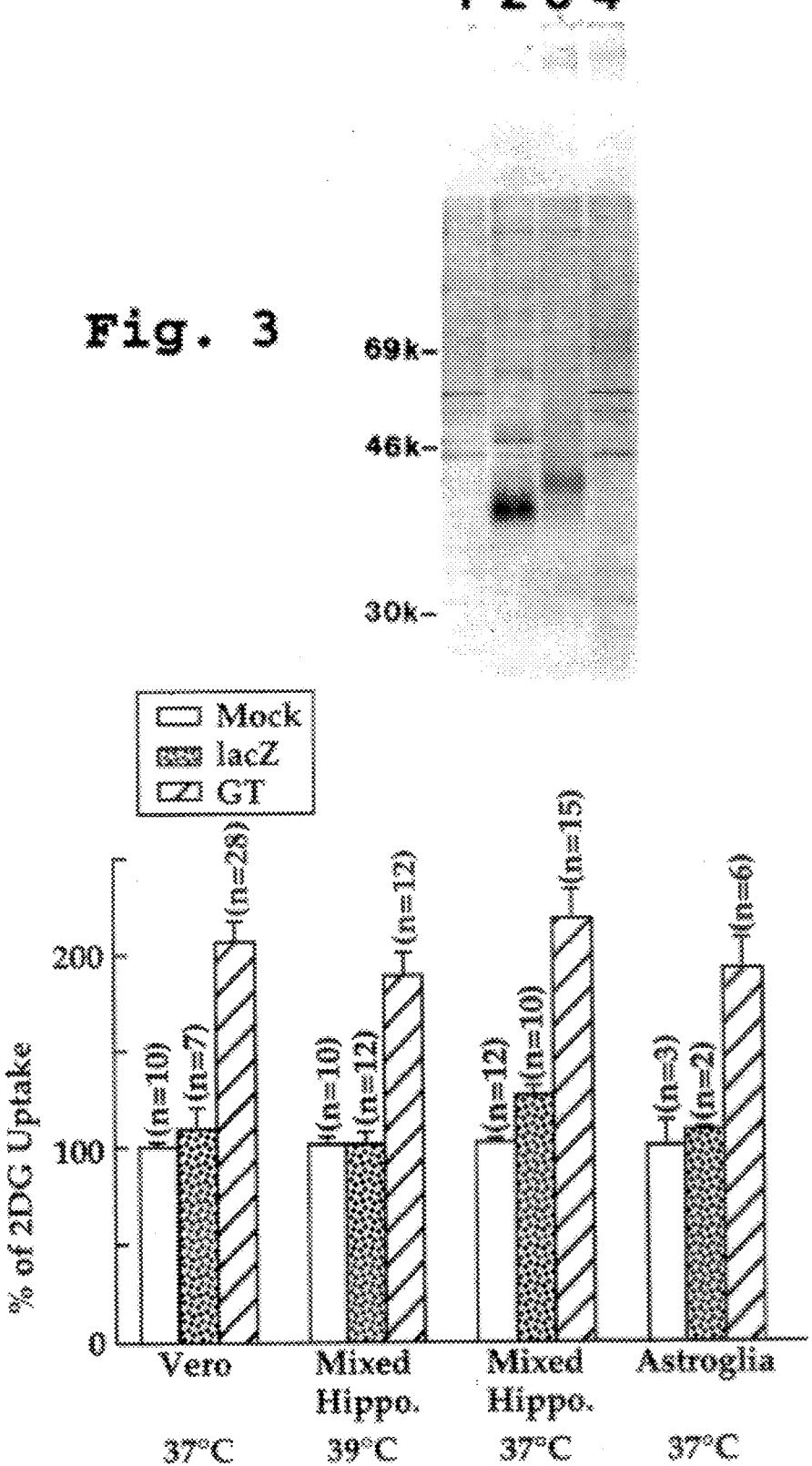
FIG. 3 is a photograph of an autoradiogram which shows the detection of glucose transporter protein (GT) expression in Vero cells using immunoprecipitation.
FIG. 5 presents a bar graph summarizing the data illustrating the effect of introduction, into Vero cells, of the defective herpes vector derived from pIE1GT (vIE1GT) on [$^{14}$C]2DG uptake in vitro.

From cells infected with a defective virus carrying glucose transporter protein coding sequences, vIE1GT, an approximately 41 kD protein is immunoprecipitated from membrane fractions from vIE1GT-infected cells (FIG. 3, lane 3). The protein is not immunoprecipitated from mock-infected or vIE1βgal-infected control cells (FIG. 3, lanes 1 and 4, respectively). In the presence of tunicamycin, this product is reduced to about 38 kD (FIG. 3, lane 2), which is the reported size of the primary translation product of GT (Glut-1 isoform; Birnbaum et al., 1986). The endogenous GT in rat brain endothelium is known to be heterogeneously glycosylated with mean molecular weight of about 52 kD (Pardridge et al.), and alternative GT species, 45–47 kD in size, also occur in rat brain (Birnbaum et al., 1986; Pardridge et al.). Thus, the 41 kD GT observed in Vero cells probably results from differential glycosylation in the Vero cells.

B. GT Expression in Infected Neurons and Astrocytes.

Figure 4A:
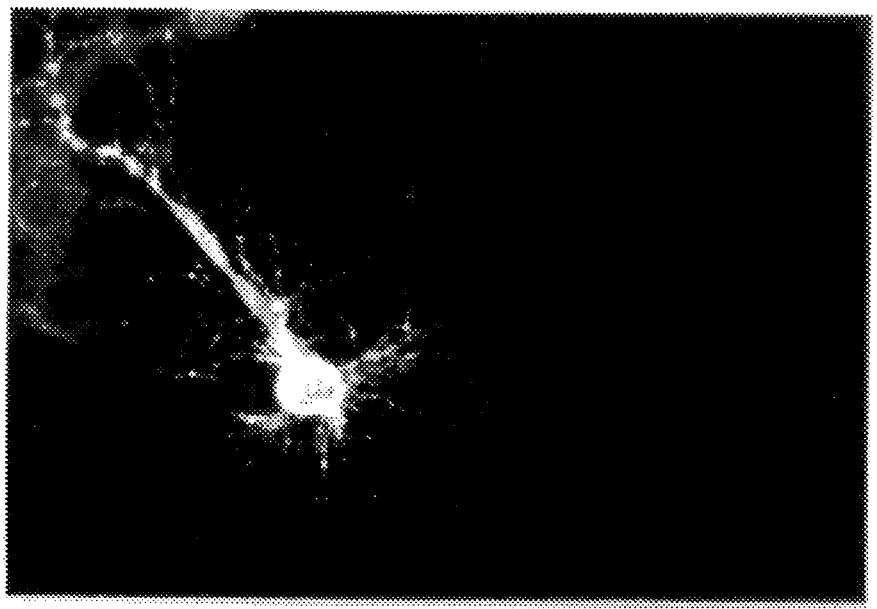
FIGS. 4A to 4D show results illustrating the co-localization of GT with neuron-specific microtubule-associated protein (MAP2) or glial fibrillary acidic protein (GFAP) antigens using double-indirect immunofluorescence.
Figure 4B:
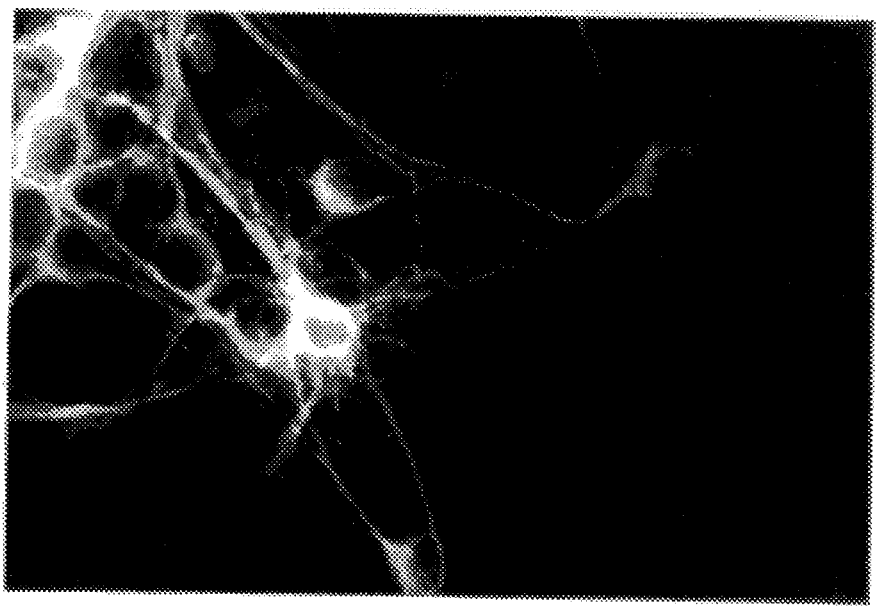
Figure 4C:
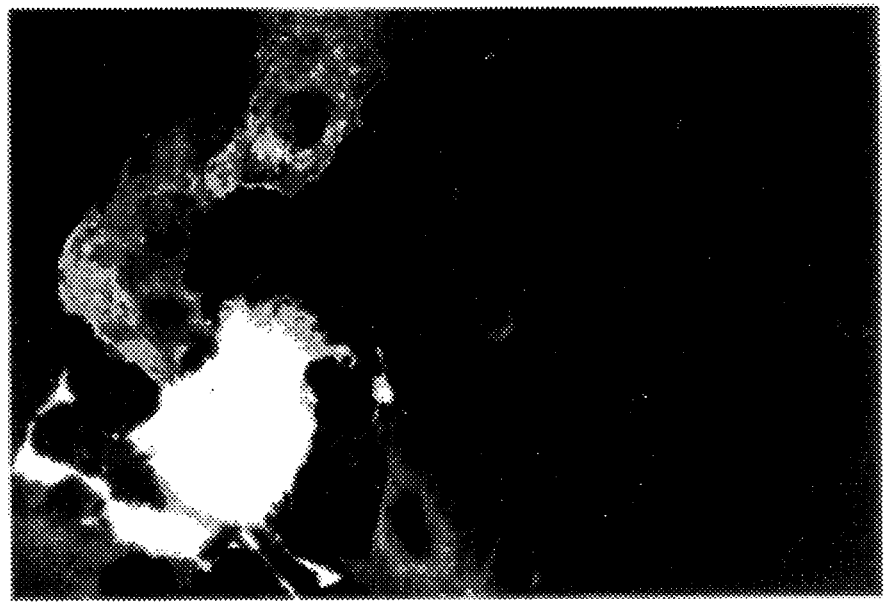
Figure 4D:
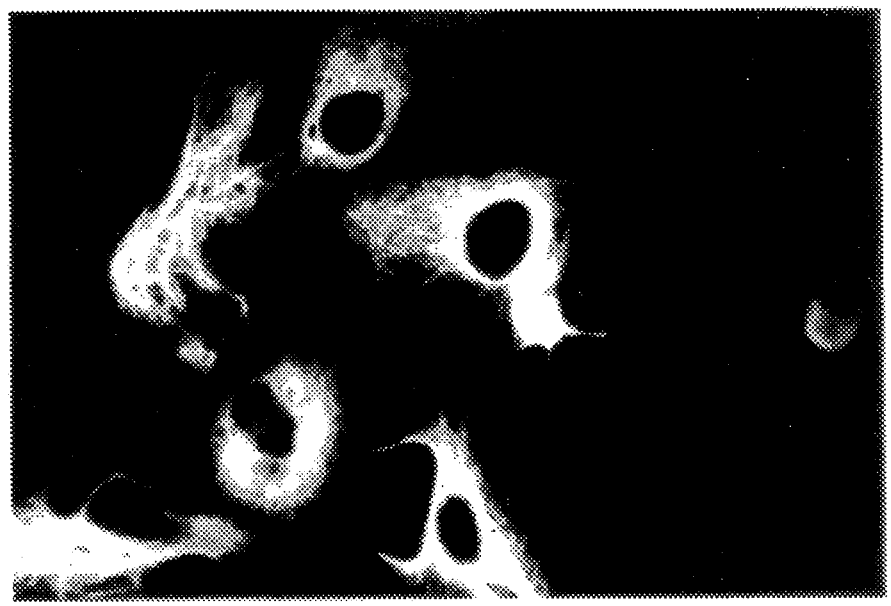

The ability of a defective herpes virus vector, carrying glucose transporter protein coding sequences, to express GT in primary cultures of hippocampal neurons and astrocytes is also examined. Expression is investigated in situ using immunofluorescence (Example 5). GT immunoreactivity is observed in cultures infected with vIE1GT (FIG. 4), but not vIE1βgal-infected or mock-infected cultures. Ten day old mixed neuronal/glial cultures from hippocampus are infected with vIE1GT for 16 hr (Example 5) and then fixed with chilled acetone/methanol (3:1). FIGS. 4A and 4B show cells which are double-stained with anti-GT serum (a) and anti-MAP2 monoclonal antibody (b). FIGS. 4C and 4D show cells which are double-stained with anti-GT serum (c) and anti-GFAP monoclonal antibody (d). The secondary antibodies are labelled with rhodamine (for anti-GT serum) and with fluorescein (for anti-MAP2 and anti-GFAP antibodies), respectively.

The double-immunofluorescence methods show co-localized expression of the neuron-specific microtubule-associated protein (MAP2) or glial fibrillary acidic protein (GFAP) with GT immunoreactivity: both neurons (FIG. 4A) and astrocytes (FIG. 4C) are capable of expressing GT. Similarly, βgal-expressing neurons or astrocytes are observed only in vIE1βgal-infected, but not in vIE1GT-infected or mock-infected cultures.

The number of cells expressing GT or βgal depends on the defective vs. helper ratio of the particular passage of viral stocks and the MOI employed. When a very high MOI is used, (e.g. MOI≧10 p.f.u. per cell), the proportion of cells in the culture expressing GT or βgal approaches 100%.

The ability of other herpes based vectors, which carry neuroprotective gene coding sequences, can be evaluated as described above for their ability to infect and express neuroprotective genes in neuronal and glial cells.

C. Effect of Infection of Cells with a Vector Carrying GT Coding Sequences on Metabolism and Neuronal Death In Vitro.

The effects of viral vector GT expression on metabolism and survival of neuronal/glial cultures exposed to hypoglycemic conditions is determined as detailed in Example 9. Cells exposed to hypoglycemic conditions typically exhibit a substantial decrease in metabolism followed by cell death of the neurons (Siesjo).

Figure 11:
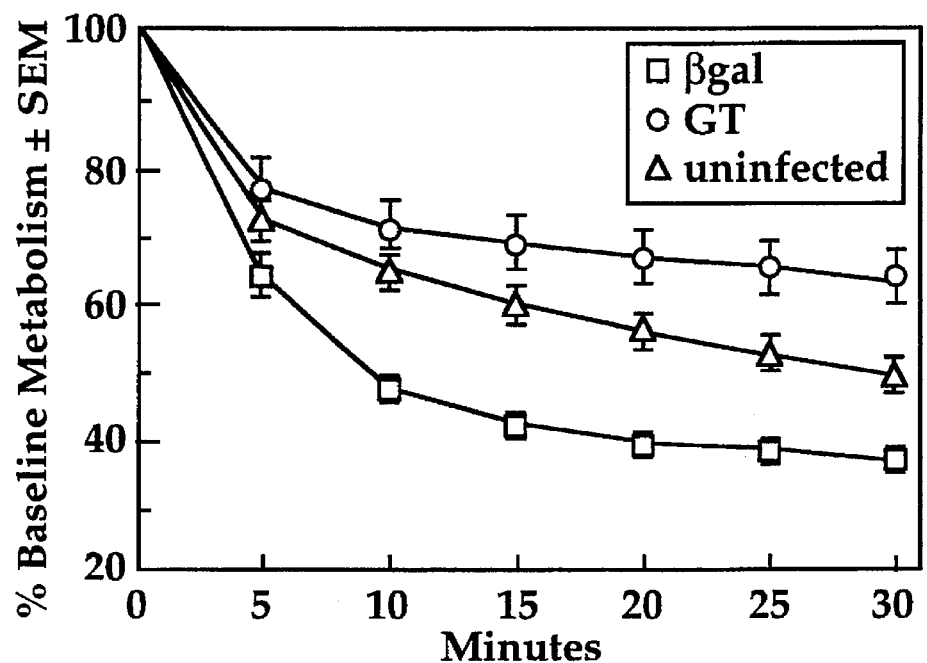
FIG. 11 shows the change in metabolic rates of mixed neuronal/glial hippocampal cultures infected with indicated vectors and exposed to hypoglycemic conditions at time zero.
Figure 12:
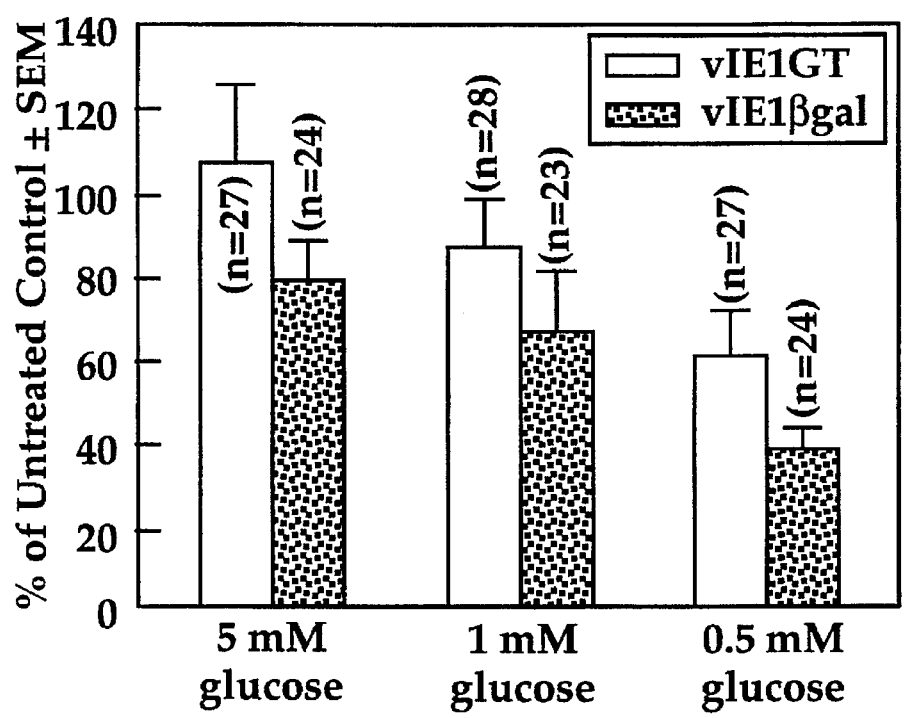
FIG. 12 shows the percent of neurons surviving in hyperglycemic mixed hippocampal cultures 8 hours after the medium bathing the cultures was changed to one containing the levels of glucose indicated, for cultures infected with either vIEGT or vIEβgal.

Experiments were performed to determine if infection by GT-expressing virus was effective to inhibit the decrease in metabolism and cell death following exposure to hypoglycemic conditions. Infection by GT-expressing virus (vIE1GT) resulted in resistance to an energetic insult, as measured by an attenuation in the decline of cell metabolism (FIG. 11) as well as the extent of neuron loss (FIG. 12). Infection by β-gal-expressing virus (vIE1βgal) or mock-infection either had no effect on the decline in cell metabolism, or accelerated the decline.

D. Effect of Infection of Cells with a Vector Carrying GT Coding Sequences on Glucose Uptake In Vitro.

The following experiments performed in support of the present invention demonstrate that cellular function can be manipulated using the vectors of the present invention. Increased GT expression was demonstrated to be associated with an increased rate of glucose transport.

Vero cells, astrocytes and mixed hippocampal cultures were plated in 48-well plates and mock-infected or infected with defective vectors at 37° C. or 39° C. as described in Example 6A. Uptake in vIE1GT-infected cultures (FIG. 5) differed significantly from mock and vIE1βgal-infected cultures ($p<0.001$ for all cases except astroglia, where $p<0.05$; Newman-Keuls post-hoc test following analysis of variance; where n averaged 10 among the various groups). Infection with vIE1GT doubled the rate of [$^{14}$C]2DG transport in Vero cells, mixed hippocampal cultures, and primary astrocyte cultures (FIG. 5). Similarly, vα4GT and vα22βgalα4GT approximately doubled glucose uptake in hippocampal cultures. Mock infection or infection with vIE1βgal did not alter transport.

E. Reversal of Glucocorticoid Effects on Glucose Uptake by Introduction of Glucose Transporter Protein Coding Sequences.

Glucocorticoids (GCs), adrenal steroid hormones released during stress, have long been recognized for their capacity to inhibit glucose transport in numerous tissues. Recent work has shown this effect to occur in the hippocampus, and in cultured hippocampal neurons and glia (Kadekaro et al.; Horner et al., 1990; Virgin et al.). The ability of glucose transporter protein coding sequences, introduced by infection, to alleviate the effect of GCs on glucose transport was tested (Example 6B).

Figure 6:
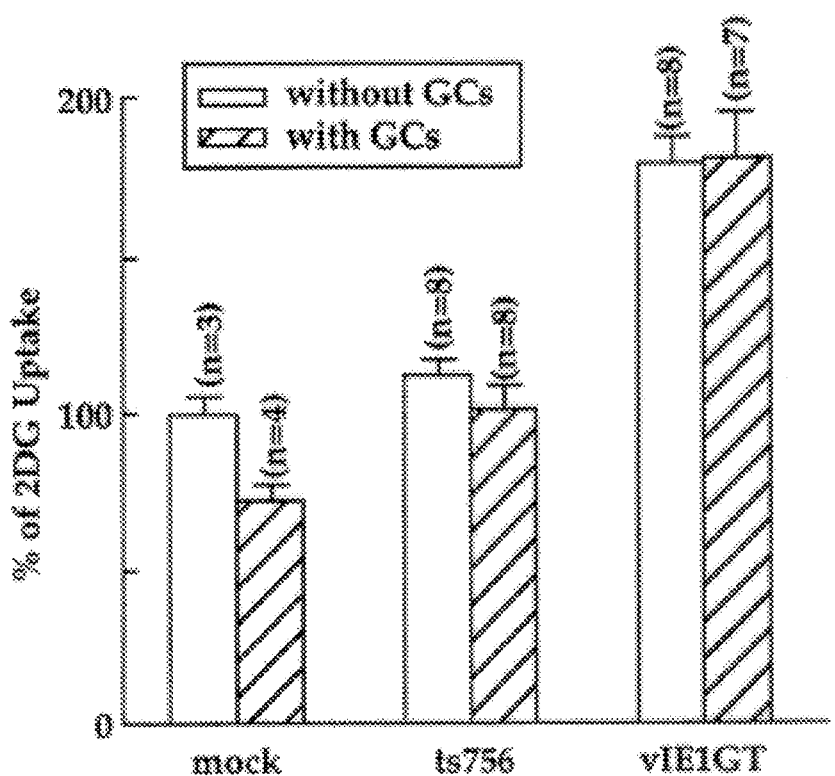
FIG. 6 presents a bar graph summarizing the data illustrating the effect of vIE1GT infection and/or glucocorticoid treatment on glucose transport.

Mixed neuronal/glial cultures from hippocampus were mocked-infected, infected with ts756 or with vIE1GT, with or without the treatment of corticosterone ($10^{-6}$M). Rates of [$^{14}$C]2DG uptake were measured at 16 hr post infection (FIG. 6). As with the experiments described above, vIE1GT infection caused a significant enhancement of glucose uptake in GC-free cultures, relative to mock-infected cultures ($p<0.001$, Newman-Keuls test). Glucocorticoid exposure caused a significant decline in glucose uptake in mock-infected cultures ($p<0.001$) but did not alter uptake rates in vIE1GT-infected cultures ($p>0.10$).

The results presented in FIG. 6 show that, while corticosterone, the principle GC of rat, inhibited about 30% of glucose uptake in mock-infected cells in agreement with previous studies (Horner et al., 1990), exposure to vIE1GT, i.e., the introduction of glucose transporter coding sequences into the cells, increased glucose transport in hippocampal cultures regardless of corticosterone treatment. Expression of GT from the amplicons is not likely to be influenced by the presence of GCs, insofar as the HCMV ie1 promoter employed to express the GT gene does not contain a glucocorticoid responsive element.

III. In Vivo Results.

A. In situ Hybridization Studies of Gene Expression from Vectors vIE1GT and vIE1βgal.

The ability of vIE1GT and vα4GT to express GT when injected into the hippocampus of adult rats was tested using in situ hybridization techniques. Positive hybridization signals were readily detected in hippocampus microinfused with vIE1GT (FIG. 10A), vIE1βgal (FIG. 10B) or vα4GT (FIG. 10C); in contrast, no such signal was detected after injection with the helper virus or with DMEM alone. The positive signals were clustered around the injection site and highly concentrated along the dorsal blade of the dentate gyrus. The pattern of vIE1βgal expression as visualized by in situ hybridization was similar to that visualized by histochemical staining with X-gal (Ho, D., et al., 1988; see below and FIG. 15).

These results support the findings presented in the section above that the glucose transporter protein coding sequences, which are carried in the herpes-based vectors, are expressed in rat brain tissue transfected with the vectors.

B. The Effect of Infection on Glucose Uptake In Vivo.

In order to determine if the delivery of recombinant coding sequences to neurons had been efficacious in altering cell physiology, the effects of introduction of the coding sequences were evaluated in vivo. For example, the effect on glucose uptake by infection of the CNS of adult rats with vIE1GT was examined.

Defective viruses were introduced into hosts via microinfusion. An alternate route of infection with the defective viruses of the present invention is interocerebroventricular (ICV) inoculation.

Figure 7:
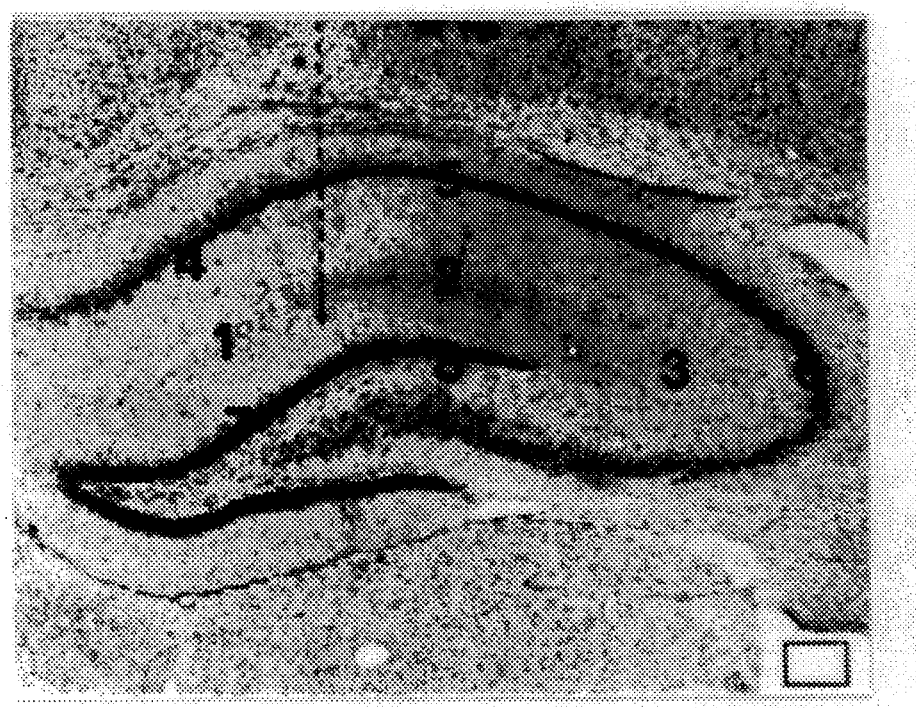
FIG. 7 shows a representative coronal section of the rat brain hippocampus showing the eight individual regions in hippocampus where glucose uptake was measured. The rectangle in the lower right corner represents the approximate area of measurement in each region.

Example 7 describes infection using the defective virus, vIE1GT, by microinfusion. vIE1GT was microinfused unilaterally into the hippocampus and vIE1βgal was microinfused contralaterally. FIG. 7 shows a representative coronal section of the hippocampus showing the eight individual regions where glucose uptake was measured. The contralateral infusion sites were used as comparison controls for the unilateral infusions sites.

Average $^{14}C$ levels in each hippocampal region was determined in 25 sections anterior and posterior to the injection site; data were pooled for areas (indicated in FIG. 7) 1, 4, and 7; areas 2, 5, and 8; and areas 3 and 6. The data, presented in FIG. 8, were derived by averaging uptake in each region 0.5 mm anterior and posterior to the injection site. Uptake in the vIE1GT injected hippocampus is expressed as percentage of uptake in the contralateral vIE1βgal control. The results of a medial/lateral analysis, presented in FIG. 8, demonstrate that [$^{14}C$]2DG uptake was significantly enhanced in vIE1GT-injected sites, relative to vIE1βgal-control ($p<0.01$, Newman-Keuls test following analysis of variance) in hippocampal regions near the site of vIE1GT injection.

Figure 9:
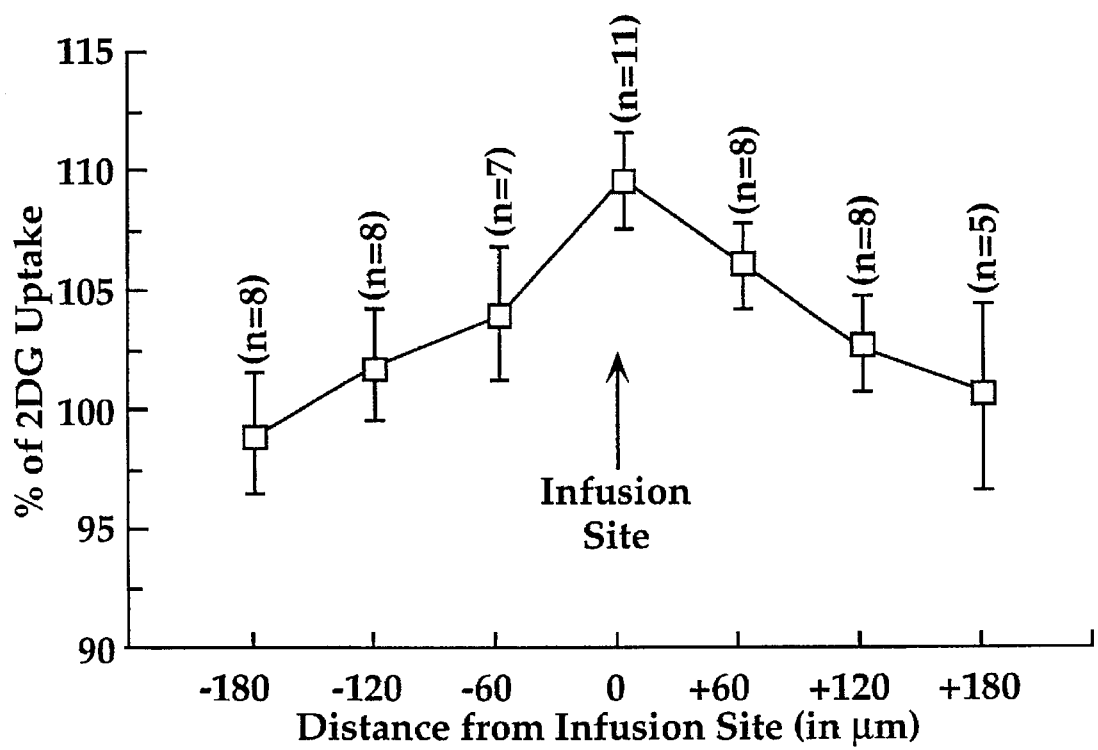
FIG. 9 presents the data of a anterior/posterior analysis showing that [$^{14}$C]2DG uptake was enhanced nearest to the site of injection of vIE1GT. Uptake (relative to the contralateral side) is shown in hippocampal region 1 as a function of distance from the injection site in the anterior/posterior plane.

The results of anterior/posterior analysis are presented in FIG. 9. Uptake (relative to the contralateral infusion site) is shown in hippocampal region 1 as a function of distance from the injection site in the anterior/posterior plane, with data pooled for every three 20 μm section. When uptake within each region was analyzed along an anterior/posterior gradient, the greatest increase in [$^{14}C$]2DG uptake was detected around the infusion site. These results suggest that [$^{14}C$]2DG uptake was enhanced nearest to the site of injection of vIE1GT.

Experiments performed in support of the present invention support that nerve cell physiology can be influenced in vivo by the introduction of protein coding sequences, such as neuroprotective gene coding sequences (e.g. sequences encoding the glucose transporter protein).

Considerable information is available as to the time-window with which neurological insults, such as hypoxia-ischemia (e.g. stroke), seizure, trauma, hypoglycemia and neurodegenerative disease, irreversibly commit neurons to damage. Thus, by knowing how quickly infection results in the expression of neuroprotective genes, the latest possible time post-insult to carry out this intervention can be determined. Experiments described below, particularly with reference to Example 12, demonstrate that the expression of a neuroprotective gene, such as GT, is rapid enough that the viral vector may be administered one hour following a neurological insult and still result in significant levels of neuroprotection.

C. Measurement of Glucose Transporter Number in Infected Cells.

The specific number of GT protein molecules expressed in infected cells can be determined by measuring the number of binding sites for cytochalasin B, an inhibitor of glucose transport that binds competitively to the GT. Specific binding is determined, and maximal binding sites and affinity of binding determined by Scatchard analysis.

Determination of GT number is conducted essentially as described by Cushman, et al. (1980), in which glucose-inhibitable cytochalasin B binding sites are measured in plasma membrane; cytochalasin B specifically inhibits the glucose transporter by binding to it. Tissue is washed and homogenized at 24° C. in 20 mM Tris-HCl, 1 mM EDTA and 255 mM sucrose and centrifuged at 16,000 g for 15 minutes at 4° C. The supernatant is discarded and the pellet resuspended, spun for 60 minutes at 23,000 g on a discontinuous 1.12M sucrose gradient in 210 mM Tris-HCl, 1 mM EDTA. The plasma membrane band is washed twice in buffer and centrifuged at 48,000 g, and resuspended to a final concentration of 3–5 mg protein/ml.

Glucose transporter in the plasma membrane is then measured with 3H-cytochalasin B at 4° C. Cytochalasin E solution (40 μl) is added to each incubation vial containing 500 μl of membrane suspension, in order to block cytochalasin B binding to sites other than the glucose transporter. In the absence of cytochalasin E, nearly 95% of cytochalasin B binding is to these other sites. 100 μl aliquots of this are then incubated with from 0.04 to 20 nm 3H-cytochalasin B; non-specific binding is assessed by parallel incubations with 250-fold excess of sucrose. The membrane suspension is then spun for 20 minutes at 48,000 g, the supernatant discarded and the pellet and tube placed in a scintillation vial for counting of bound 3H-cytochalasin B. Binding is expressed as per mg protein.

The determination of the number of GT protein molecules provides a method of evaluating and comparing the level of GT produced as the result of infection using different defective viruses, carrying glucose transporter coding sequences. Thus providing a way to select vectors that have optimized GT production in host cells.

This procedure can also be used to determine the number of GT protein molecules expressed by cells in culture.

D. Expression of Vector-Encoded Genes in Rat Hippocampus.

Figure 15:
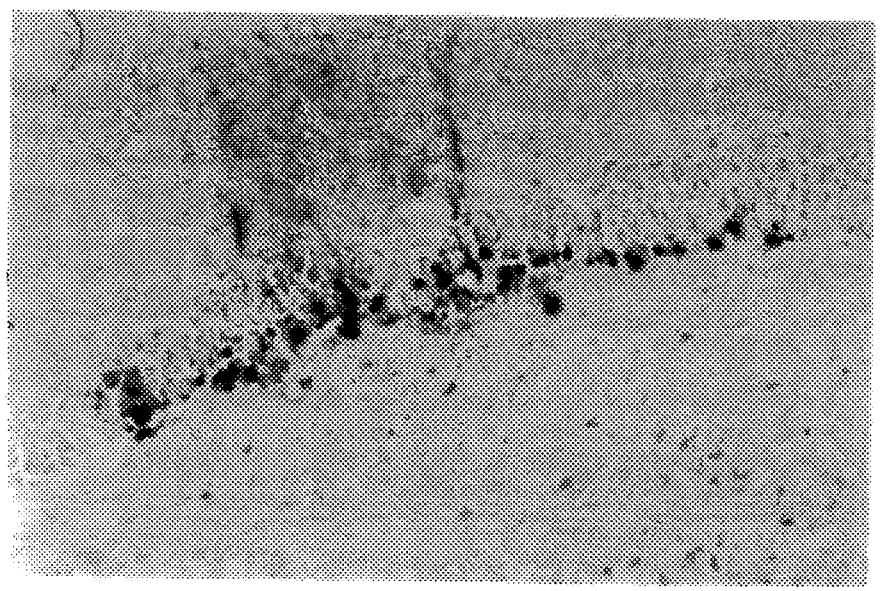
FIG. 15 shows patterns of gene expression in hippocampus from vector vIE1βgal as detected by X-gal staining.
Figure 16A:
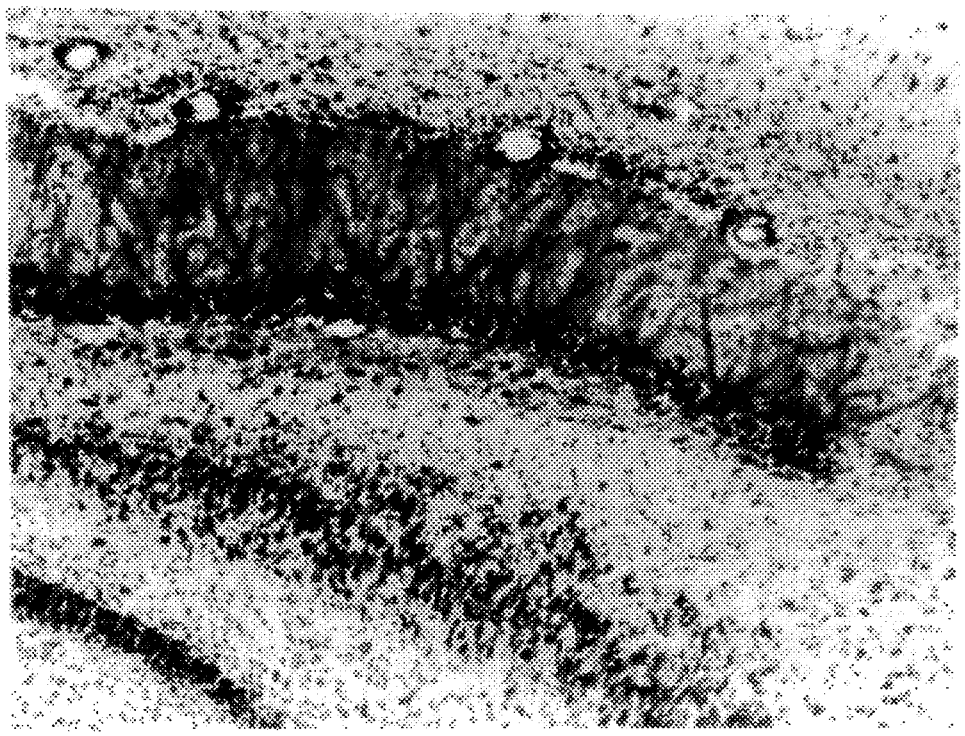
FIGS. 16A and 16B show vα22βgalα4GT expression in the dentate in X-gal/cresyl violet stained sections at 20× (FIG. 16A) and 40× (FIG. 16B) magnification.
Figure 16B:
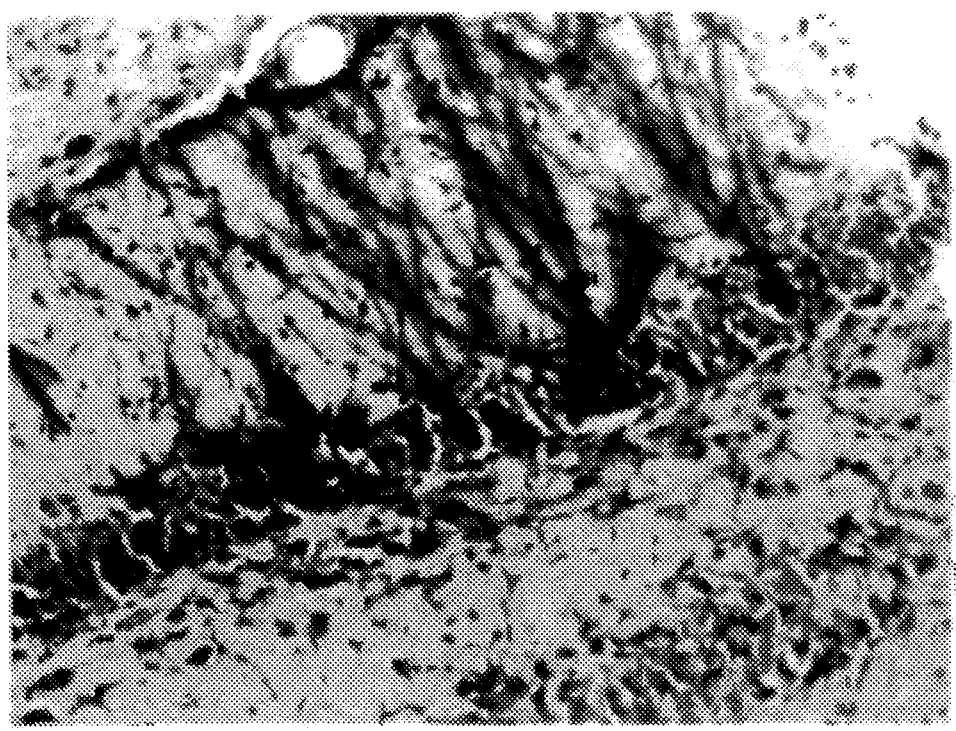

To assess the level of vector-encoded gene expression in vivo, rats were microinfused in their hippocampi with either vIE1GT or vα22βgalα4GT, sacrificed and brains were frozen, sectioned and stained as described in Example 11. Exemplary micrographs are shown in FIGS. 15, 16A and 16B. FIG. 15 shows patterns of gene expression in hippocampus from vector vIE1βgal as detected by X-gal staining (compare to in situ hybridization of expression of the same vector in FIG. 10B). FIGS. 16A and 16B show vα22βgalα4GT expression in the dentate in X-gal/cresyl violet stained sections at 20× (FIG. 16A) and 40× (FIG. 16B) magnification.

E. Protection of Neurons from KA-induced Seizures.

Kainic acid (KA) initiates seizures when infused into the brain, and is commonly used as a model of neuronal injury or insult. KA endangers neurons by triggering an excitotoxic cascade that results in the accumulation of excitatory amino acid neurotransmitters (EAAs) and subsequent elevation of free cytosolic calcium. Under such circumstances, more energy availability (for example, as a result of enhanced glucose uptake) translates into an enhanced capacity to control the release and reuptake of EAAs, as well as the sequestering and efflux of cytosolic calcium.

Experiments performed in support of the present invention demonstrate that viral vectors of the present invention are effective to inhibit or reduce CNS damage due to neuronal insults, such as KA-induced seizures, in vivo. Example 12 details studies where control or GT-expressing vectors are microinfused into the hippocampi of rats either prior to, simultaneously with or after infusion of KA. Lesions caused by KA-induced seizures are measured and compared between GT-infected and control sections.

Figure 17A:
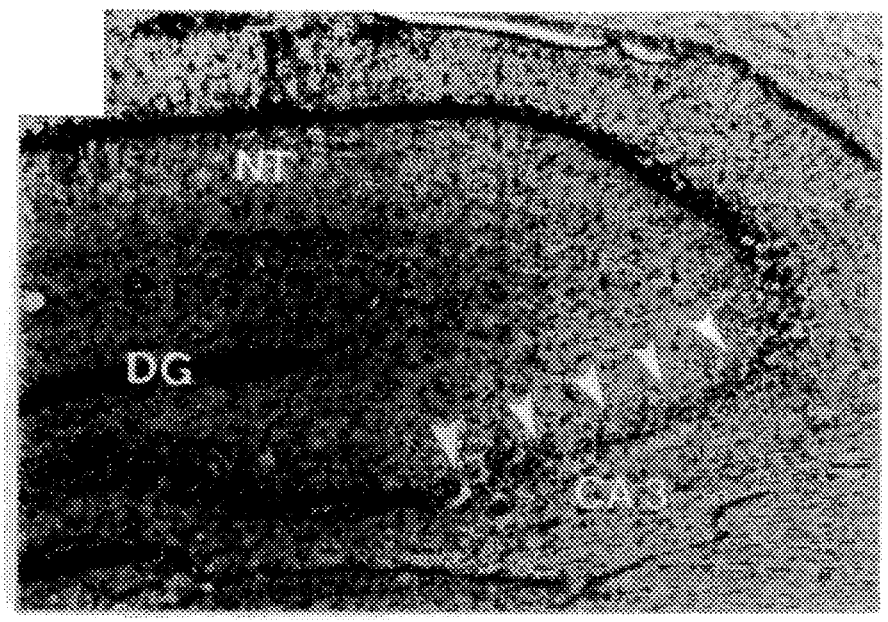
FIGS. 17A and 17B show CA3 hippocampal cell fields following infusion of KA alone (FIG. 17A) or KA with vα4GT (FIG. 17B). The lesion (arrows) measured 0.91 mm in the control field (FIG. 17A) and 0.54 mm in the vector-treated field (FIG. 17B).
Figure 17B:
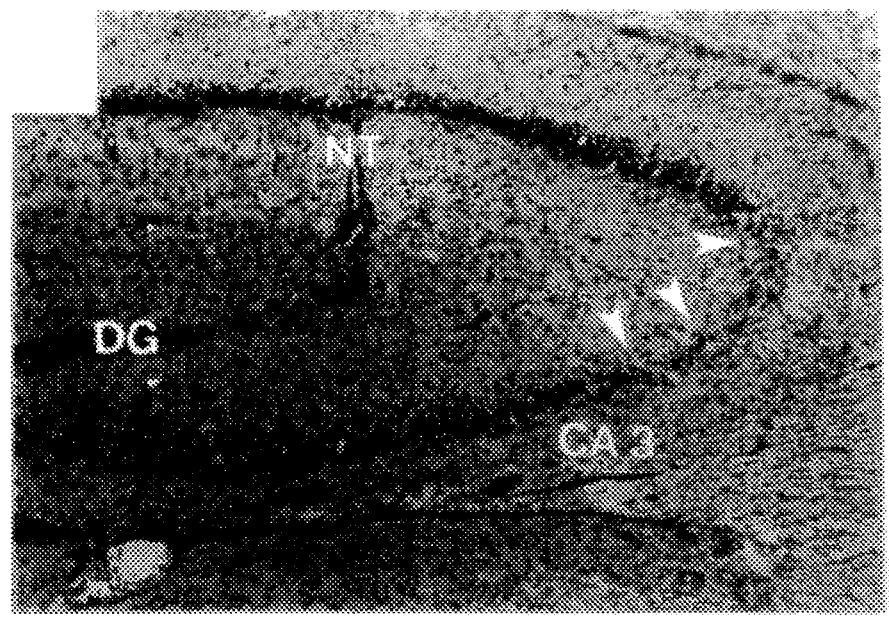
Figure 18:
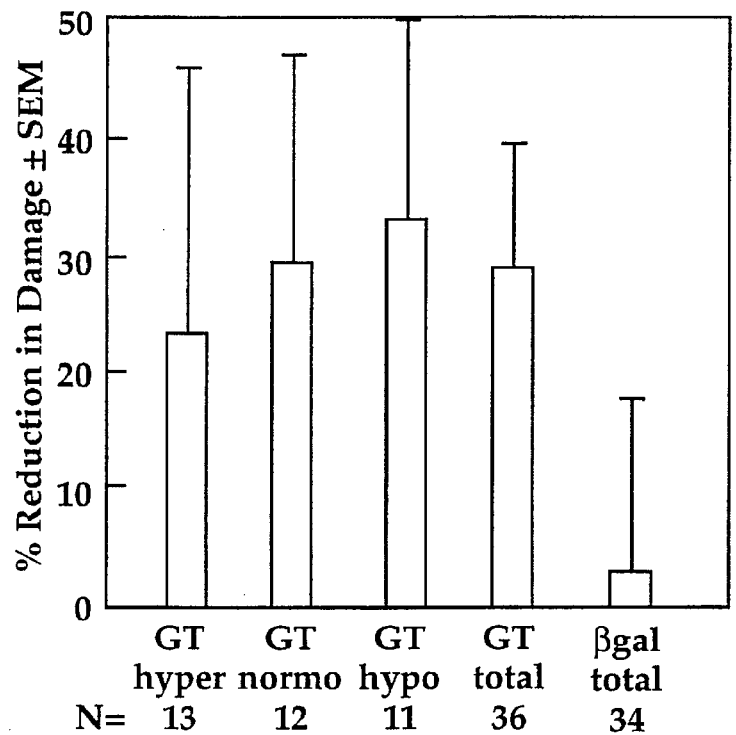
FIG. 18 shows the percent reduction in KA-induced damage in hyper-, normo- and hypo-glycemic rats by infection with vα4GT or vα4βgal.

The results are illustrated in FIGS. 17A, 17B, 18, 19 and 20. When vα4GT, but not vα4βgal, is unilaterally microinfused into the hippocampus 12 hours before bilateral infusion of KA (which damages CA3 pyramidal neurons in a pattern resembling human status epilepticus (Ben-Ari, 1985)), there is a significant reduction in the size of the lesion as compared to the contralateral uninfected cell field (FIGS. 17A and 17B). The degree of protection quantitated as described in Example 12, is significant in hypoglycemic and normo-glycemic rats (FIG. 18).

To determine whether viral intervention is neuroprotective following a seizure rather than in anticipation of it, vα4GT was delivered at 0, 1 or 4 hrs after KA infusion. Significant protection occurred at the 0 and 1 hr time points (FIG. 19). vα4βgal did not confer protection at any time.

As discussed in Example 11, microinfusion of $4 \times 10^3$ vα4βgal virions resulted in the infection of 725±44 neurons, indicating that approximately 18% of infused virions successfully infected neurons. Therefore, microinfusion of vectors, even at considerably higher titers, would be expected to target a subset of neurons in a kainic acid (KA)-endangered hippocampal cell field. In this context, the extent of protection observed is greater than may apparent from a cursory review of the data, suggesting that, due to the extensive collateralization, metabolically bolstering a single dentate neuron may protect multiple CA3 pyramidal neurons.

The hippocampal protection is particularly noteworthy in terms of the time of vector delivery. vα4GT infection results in gene expression within 4 hours and peaks within 8 hrs. Thus the protection observed by the delivery of the vector 1 hr after KA represents an actual protective effect of GT-overexpression several hours after the onset of the insult. Such delayed protection agrees with the observation that the mediators of excitotoxic neuron death emerge gradually over the course of hours.

F. Correlation of β-gal Expression with Neuronal Damage Reduction.

Figure 20:
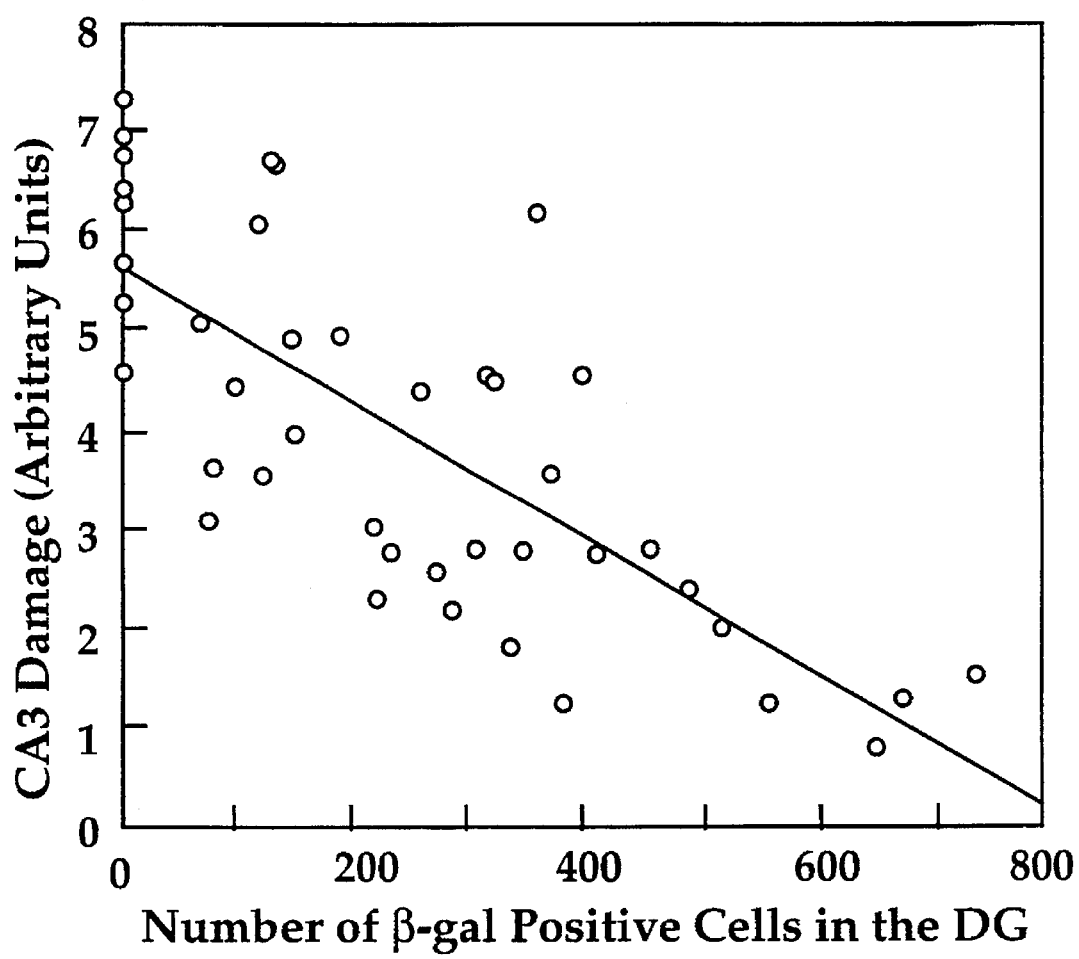
FIG. 20 shows a correlation comparison of the number of β-gal positive cells in the dentate gyrus with the degree of damage in CA3.

To explore the relationship between the actual location and extent of viral infection and the resulting level of protection, the bicistronic vector vα22βgalα4GT was microinfused as described in Example 12B. Delivery of this vector allowed both the identification of infected neurons through X-gal staining (the majority of which were again in the dentate) and an assessment of the extent of seizure-induced damage. When vα22βgalα4GT and KA were delivered simultaneously, an inverse correlation between the number of β-gal-positive neurons in the dentate and the amount of CA3 damage was observed (FIG. 20). The level of expression of the control vector, vα22βgalα4gts, in the dentate showed no correlation with damage.

IV. Applications.

The results presented herein describe the successful delivery of a functional eucaryotic gene into neurons in culture and into adult mammalian CNS using the defective HSV vector system. Both in vivo and in vitro, vIE1GT enhances the rate of glucose transport and makes cultured cells resistant to the inhibitory effects of GCs upon glucose transport. The vector also inhibits the decrease in metabolism and cell death following exposure to hypoglycemic conditions. Furthermore, infection with the GT-encoding vectors vα4GT and vα22βgalα4GT results in significant neuroprotection, even when the vector is administered one hour after the neurological insult. This scenario is relevant to clinical situations, in which the occurrence of the neurological crisis cannot be predicted in advance. The neuroprotection afforded by infection with the virus is most likely due to expression of the viral vector, since a an inverse correlation was observed between the number of β-gal-positive neurons in the dentate and the amount of CA3 damage (using vα22βgalα4GT).

Viral vectors of the present invention are also effective at reducing neuronal cell death in striatal cultures treated with the neurotoxin 3-nitroprionic acid. This toxin is believed to provide a good model for the damage that occurs in the striatum in Huntington's disease (Beal, 1992). Further, the constructs are effective to protect neurons in hippocampal and spinal cord cultures against glutamate- and hypoglycemia-induced damage, an in vitro model for ischemic damage (Choi, 1988a).

The results described in the above sections, suggest that intervention with a herpes virus vector carrying glucose transporter protein coding sequences may be used to enhance glucose transport into neurons and thus make infected neurons more resistant to excitotoxic insults. In many neurological disorders such insults arises from excessive excitatory amino acids (EAAs), such as glutamate. EAAs and neurological disorders involving EAA excess deplete neurons of energy substrates, and the toxicities of these insults are energy-dependent. Such disorders include, but are not limited to, Huntington's disease, hypoxia-ischemia, seizure, hypoglycemia and trauma. Excessive EAAs cause pathologic mobilization of free cytosolic calcium, with numerous degenerative consequences: one theme common to excitotoxic insults is that they constitute crises of energy.

Glucocorticoids (GCs) exacerbate the EAA/calcium cascade. Glucocorticoids (i) impair glutamate uptake (Halpain, et al.), (ii) increase free cytosolic calcium mobilization following EAA exposure (Elliot et al., 1990), (iii) enhance extracellular EAA concentrations during seizure, and (iv) augment calcium-induced proteolysis of cytoskeletal proteins. The energy-dependency of these steps is demonstrated by the fact that these effects can be prevented with energy supplementation.

Glucocorticoid enhancement of excitotoxicity supports the premise that energy depletion hastens neuron death. In particular, the glucocorticoid endangerment appears to arise from the ability of the steroid to disrupt neuronal energetics and exacerbate steps of the EAA/calcium cascade. The extent of glucose transport into affected neurons appears to be an important metabolic bottleneck during GC mediated neurological insults.

Experiments performed in support of the present invention suggest that the buffering of neurons from energetic disruption, which results from the above insults, may be used to protect the affected cells from damage. The protection is conferred by increasing energy availability in affected cells, e.g., by introduction of sequences expressing glucose transporter protein into these cells. The defective viruses described above provide the basis for intervention with a herpes virus vector in order to make neurons more resistant to excitotoxic insults. Specifically, the gene for the glucose transporter (GT) is inserted into neurons, in order to cause overexpression of the protein and increased hexose transport into cells. By this means, neurons will be metabolically-buffered during these insults.

As an additional or alternative route of neuroprotection, ascorbate appears to be taken into various peripheral cell types via the glucose transporter (Boast, et al., 1987; Boast, et al., 1988; Gill, et al., 1988; Levy and Lipton, 1990). If infection with GT-bearing vectors enhances uptake of this antioxidant, this manipulation would bolstered defenses against the oxygen radicals known to be central to excito-toxic neuron death (Coyle and Puttfarcken, 1993).

In one embodiment of the present invention, use of the herpes simplex virus type 1 (HSV-1) is an excellent vector for practicing the method of the present invention because of its natural propensity for infecting the nervous system and its ability to infect many cell types of many different species.

The ability of cells expressing glucose transporter protein to resist neurological insults is evaluated as follows. The neurotoxic effects of EAAs in the striatum (probably the most credible of rat models for Huntington's disease) and in the hippocampus (as a model for excitotoxic seizures) are example model systems.

In the Huntington's disease model, striatal infusions are made of kainic acid, ibontenate and of quinolinate. These compounds, collectively, are the most efficacious EAAs in mimicking the neurodegenerative features of Huntington's disease (Kowall et al.). In the hippocampal seizure model, infusions of kainic acid, glutamate and NMDA are made.

The neurochemical consequences of these insults in control and experimental rats are studied. Specifically, it is determined if in experimental rats, these insults are associated with (a) less of a decline in phosphocreatine and ATP concentrations, and (b) less intracellular accumulation of calcium. Calcium trafficking is studied with microdialysis of Ca-45 (Elliot, et al.).

Another model to which GT-encoding vectors of the present invention are applied is in vivo neuronal protection against 3-Nitroprionic acid. In this model of Huntington's disease, rats are microinfused unilaterally in the striatum with a GT-encoding vector and a helper virus through stereotaxically-implanted cannulae. The contralateral cell field receives an injection of virus-free DMEM. Vector is delivered either before, simultaneously with or after bilateral delivery of 3-nitroprionic acid. Animals are sacrificed and brains are fixed, sectioned and stained essentially as described in Example 12. Lesions are measured and quantitated as described above.

In a hypoglycemia model, rats are microinfused bilaterally in the hippocampus with either a GT-encoding or control vector and unilaterally with the toxin 3-acetylpyridine, an antimetabolite that mimics hypoglycemic damage. The animals are sacrificed and brain sections prepared as described above. The sections are analyzed and the extent of damage induced by the toxin, either in the presence of the GT-encoding or the control vector, is quantified.

Yet another application of the vectors of the present invention is neuronal protection against stroke. An accepted animal model of stroke is the occlusion of the middle cerebral artery in rats. In a demonstration of this application, rats are microinfused bilaterally with a GT-encoding or control vector as described above, except the infusion is into the cortex and the striatum. One hour later, a stroke is induced unilaterally by occluding the middle cerebral artery. The stroke maintained for two hours. Two days later, animals are euthanized and the extent of damage in vector-positive neurons quantified.

Some other models that are of relevance include models motoneuron death in amyotrophic lateral sclerosis (ALS), concussive trauma to the spinal cord, and the apoptotic photoreceptor death seen in retinitis pigmentosa. Further, viral vectors of the present invention that express stably over time may be effective to slow down the normative neuron death during aging, and HIV-induced neuronal damage.

The above-described studies provide defective viral vectors which provide a means of somatic gene therapy to alter neuronal function and protect neurons from insult. The brain is exquisitely dependent upon glucose; nervous tissue has extremely high metabolic rates, utilizes little other than glucose and stores it poorly (Siesjo). Moreover, neurological insults such as hypoxia-ischemia, hypoglycemia and sustained seizure disrupt energy charge in the brain and preferentially damage the hippocampus; in the case of sustained seizure, glucose transport can become the rate-limiting step determining whether there is a damaging mismatch between energy delivery and utilization (Auer et al.).

Neuron death typically emerges slowly over the 48–72 hours following the neurological insults described above. As demonstrated herein, exposure of the hippocampus to, for example, v$\alpha$4GT, even one hour following onset of the insult results in enhanced glucose transport and significant levels of neuroprotection.

Vector of the present invention may be used to introduce other genes of interest, including other genes whose expression is effective to reduce neuronal damage in response to a neurological insult, into brain tissue. Neuroprotective genes include genes encoding glucose transporter protein, apoptosis-suppressor bcl-2, calbindin D28K, superoxide dismutase (SOD) and heat shock protein 72 (HSP72).

Apoptosis-suppressor bcl-2 prevents cell death in a wide variety of circumstances (Zhong, et al.), and is now believed to work as an antioxidant (Hockenbery, et al.). Experiments performed in support of the present invention demonstrate that infection by a viral vector encoding bcl-2 reduces oxygen radical- and glutamate-induced damage in hippocampal cultures, and oxygen radical-generated damage in the hippocampus in vivo.

Further experiments performed in support of the present invention show that infection by a viral vector expressing calbindin D28K, one of the principal calcium binding proteins found in the cytoplasm, decreases resting calcium concentrations in cultured hippocampal neurons.

Superoxide dismutase (SOD), one of the main antioxidants found in cells, is also cloned into a vector construct of the present invention for use as a neuroprotectant. A mutation in SOD is likely to be the cause of familial amyotrophic lateral sclerosis (ALS, aka Lou Gehrig's disease, Rosen, et al.). Further, transgenic mice that overexpress SOD in the brain are resistant to stroke damage (Chan, et al.).

Heat shock protein 72 (HSP72) is one of a family of "stress proteins" that are induced in response to cellular stress (Welch). Many of these proteins are suitable to use with vector constructs of the present invention. HSP72 may be a particularly effective neuroprotectant when utilized in connection with the methods and compositions of the present invention.

In cases where these or other neuroprotective genes are employed, the GT gene may be used as a co-transfection marker to verify the presence of the vector in transformed brain tissue. Increased glucose transport and utilization in brain tissue can be evaluated by standard methods, including positron emission tomography (PET).

The following examples illustrate, but in no way are intended to limit the present invention.

MATERIALS AND METHODS

Statistical methods used to analyze data presented herein can be found, for example, in Zar.

All cells were maintained in a 5% $CO_2$ atmosphere.

EXAMPLE 1

Cell Cultures

A. Mixed Neuronal/Glial Cultures.

Mixed neuronal/glial cultures and enriched glial cultures were prepared from fetal Sprague-Dawley rats on the 18th day of gestation according to the method of Yu, et al., with the following modifications. Fetuses were removed from anesthetized mothers, and the fetal brains were removed and placed in 37° C. MEM-PAK, a modified minimal essential medium (Yu, et al.) purchased from the cell culture facility of University of California at San Francisco.

Hippocampi were dissected from the brains and pooled. The pooled hippocampi were washed three times with MEM-PAK and dispersed enzymatically with 2 mg/ml trypsin (GIBCO/BRL, Ground Island, N.Y.) in Hank's balanced salt solution (GIBCO/BRL) for 1 minute. Horse serum (Hyclone Laboratories, Inc., Logan, Utah) was added to the cell suspension to a final concentration of 10%.

The cells were washed once with MEM-PAK, passed through a 70 μm filter and counted. For mixed neuronal/glial cultures, cells were plated on to chamber slides or plates pre-coated with poly-D-lysine (30 μg/ml; Sigma, St. Louis, Mo.) at densities as described below. The cells were maintained in MEM-PAK supplemented with 10% horse serum.

The cells were used at about 10 days of age when the ratio of neurons versus astrocytes was approximately 50:50 as determined by immunocytochemical staining with antibodies against microtubule-associated protein (MAP2) and glial fibrillary acidic protein (GFAP) (Sigma Chemicals, Inc., St. Louis, Mo.). The antigens were detected with a Vectorstain ABC kit purchased from Vector Laboratories, Inc. (Burlingame, Calif.).

B. Glial-Enriched Cultures.

The preparation for glia-enriched cultures has been described previously (Horner, et al., 1990). The glial cultures were maintained in Dulbecco's modified Eagle medium (DMEM, GIBCO BRL) supplemented with 5% fetal calf serum (FCS, Hyclone Laboratories, Inc.).

C. Cell Lines.

Vero cells were obtained from the American Type Culture Collection (ATCC; 12301 Parklawn Dr., Rockville Md. 20852; Accession number ATCC CCL81). E5 cells were obtained as described by DeLuca, et al. Both cell types were maintained in DMEM supplemented with 10% NuSerum (Collaborative Research, Bedford, Mass.).

EXAMPLE 2

Construction of Amplicons Containing Glucose Transporter Coding Sequences

The amplicon pIE1GTori (FIG. 1A) was constructed as follows. The glucose transporter (GT) coding sequence was isolated from prGT3 (Birnbaum, et al., 1986) as an EcoRI-BglII fragment. The GT sequence was cloned into the expression vector pG310, which was obtained from Drs. Lidia Sambucetti and Edward Mocarski (Stanford University). The vector pG310 contains the promoter, exon 1 (untranslated) and intron 1 (from −1021 to +947), and the polyadenylation (polyA) signal (from +3270 to +3430) of the human cytomegalovirus (HCMV) ie1 gene. pG310 was originally constructed in a pGEM2 (Promega, Madison, Wisc.) background.

The pG310 plasmid was derived from pON308G (Cherrington, et al.) by (i) deleting the pGEM2 sequences between EcoRI and BamHI, (ii) deleting the IE1 coding sequences (exons 2–4) between the PstI site (+947) and the BamHI site (+3270), and (iii) inserting a linker with a unique EcoR1 site downstream of the splice acceptor of intron 1. The GT gene was cloned into the EcoR1 site. Transcription of GT is terminated by the ie1 polyA signal.

The HSV-1 $ori_S$ (295 bp) and the a sequence (330 bp) were then isolated as an XbaI fragment from the pON812 vector and inserted downstream of the ie1 polyA signal. pON812 (Drs. Jeffrey Viera and Edward Mocarski, Stanford University) was constructed by inserting into the cloning vector pIC-20H (Marsh et al.)—(i) the a sequence (Varmuza, et al.; Dutch, et al.), isolated from pUC18-19 (Dr. James Smiley, McMaster University) as a BamHI fragment, and (ii) the $ori_S$, isolated from pON103 (Elias, et al.) as a HindIII-EcoRI fragment.

The construction of pIE1βgalori (FIG. 1B) was similar to that of pIE1GTori, except that the glucose transporter gene and the HCMV ie1 polyA signal were replaced by a EcoRI-XbaI fragment from pON3 (Manning, et al.) containing the *Escherichia coli* lacZ gene and the polyA signal of simian virus (SV) 40.

Amplicons pIE1GTori and pIE1βgalori are referred to herein as IE1 amplicons, and were typically utilized for in vitro experiments.

The amplicon pα4GT (FIG. 2A) was constructed as follows. A BamHI fragment from pON812 containing the a sequence and a SalI-XbaI fragment from pRB3181 (Shih, et al., 1984) containing the α4 promoter (labeled ICP4 promoter in the figure) and the adjacent $ori_s$ were cloned into pGEM2 (Promega) and the resulting plasmid was named pα4a. The GT gene with the HCMV ie1 polyA signal was then isolated from pIE1GTori as an XbaI fragment and cloned into a unique XbaI site of pα4a downstream of the α4 promoter to make pα4GT.

The amplicon pα4βgal was constructed as follows. A SalI-BamHI fragment containing the α4 (ICP4) promoter and the *Escherichia coli* lacZ gene was isolated from plasmid pON105 (Ho and Mocarski, 1988) and cloned into pGEM2 (Promega Corp., Madison, Wisc.) linearized with SalI and BamHI. The resulting plasmid was then restriction-digested with BamHI and ligated with a BamHI fragment isolated from pON812 containing the a sequence. The resulting is pα4βgal.

Amplicons pα4GT and pα4βgal are referred to herein as α4 amplicons, and were typically used in vivo.

Construction of the amplicon pα22βgalα4GT (FIG. 2C) took advantage of the observation that the same DNA fragment containing the α4 promoter also contains the α22 promoter oriented in the opposite direction (McGeoch). The amplicon was constructed as follows. A 1800 bp HindIII fragment containing the opposite reading α22-α4 promoter sequences was isolated from pα4βgal and further digested with EcoNI to remove the remaining α22 coding sequences. The resulting 1100 bp fragment was re-ligated into the parent plasmid such that the lacZ gene was under the control of the α22 promoter. A 1990 bp EcoRI-BglII fragment from pIE1GTori containing the GT coding sequences of the IE1 polyA signal was inserted downstream of the α4 promoter.

The amplicon pα22βgalα4gts was constructed by deleting the GT coding sequence of pα22βgalα4GT from the 23rd to the 167th codon and further inserting a linker carrying termination codons (New England Biolabs, Beverly, Mass.) at this site. Thus pα22βgalα4gts does not make any functional GT.

Amplicons pα22βgalα4GT and pα22βgalα4gts are referred to herein as α22-α4 amplicons, and were typically used for GT/β-gal co-localization experiments.

EXAMPLE 3

Propagation of Defective HSV Vectors

The helper virus used for the propagation of the IE1 amplicons was a temperature sensitive mutant of HSV-1, ts756 (Hughes, et al.). The ts756 helper virus was typically propagated on Vero cells (Example 1) at 33° C.

To generate defective IE1 HSV vectors, 3 μg of IE1 amplicon DNA and 10 μg genomic DNA of the helper virus were transfected into Vero cells (~1×10$^6$ cells) using the calcium phosphate-glycerol shock method (Ho et al., 1988). When 100% cytopathic effect was observed, the cells were then freeze-thawed and sonicated to release the infectious virus. The resulting virus stocks contained a combination of defective virus, or viral vector (vIE1GT or vIE1βgal), and the helper virus. These stocks were then serially passaged onto fresh Vero cells after a 1:4 dilution (Spaete, et al.).

Titers of ts756 in viral stocks were determined by standard plaque assays performed at 33° C. on Vero cells. Titers of defective virus carrying amplicons were estimated by quantitating the number of cells expressing GT via immunocytochemistry using anti-GT antibodies (East Acres Biologicals, Southbridge, Mass.; Haspel, et al., 1988), or expressing β-galactosidase (βgal) via staining with X-gal (5-bromo-4-chloro-3-indolyl-galactopyranoside; Molecular Probes, Inc. Eugene, Oreg.), a chromogenic substrate for β-galactosidase (Ho, et al., 1988).

It should be noted that each defective virus carries multiple copies of the amplicon in a concatemeric form. The ratio of defective versus helper virus varied during passage but typically peaked at passage four or five with the maximal helper:defective ratio reaching about 1:1. Viral stocks from passages four or five were used. Unless otherwise stated, experiments in cell culture were performed at 37° C., a temperature that retarded ts756 growth and reduced cytopathic effects.

The helper virus used for the propagation of the α4 amplicons was a mutant of HSV-1, d120, having a deletion in the α4 gene (DeLuca, et al., 1985). The d120 helper virus was propagated in E5 cells (Example 1), which had been stably transformed with α4 (DeLuca, et al., 1985).

Defective α4 HSV vectors were generated by transfection of α4 amplicons plasmids into E5 cells using lipofectamine according to the manufacturer's protocol (Gibco BRL, Grand Island N.Y.). Briefly, amplicon DNA and lipofectamine were separately diluted in OPTI-MEM I reduced serum medium (Gibco BRL). The two solutions were then mixed, incubated at room temperature for 30 minutes, then added to E5 cells prewashed with the OPTI-MEM I medium.

After a 6-hour incubation, DMEM containing 20% NuSerum was added to the cells without removing the OPTI-MEM I medium to achieve a final NeSerum concentration of 10% (Hawley-Nelson, et al.). Twenty four hours after transfection, the cells were superinfected with the helper virus d120 at a multiplicity of infection (MOI) of about 0.1 plaque forming units (p.f.u.) per cell.

Defective virus stocks, or viral vector (vα4GT and vα4βgal), were obtained as described above and passaged onto fresh E5 cells after a 1:4 dilution. Repeated passaging gave rise to vector titers of 2–3×10$^6$ infectious particles/ml DMEM and d120 helper virus titers of 2–8×10$^6$ PFU/ml DMEM by the third or fourth passage.

pα22βgalα4GT and pα22βgalα4gts were used to obtain virus vectors vα22βgalα4GT and vα22βgalα4gts, respectively, as described above for α4 amplicons.

For in vivo microinfusion, viral vectors were concentrated 5–10-fold using microconcentrator devices with MW cutoff of 100 KD (Amicon, Danvers, Mass.).

EXAMPLE 4

Detection of Glucose Transporter Protein Expression in VERO Cells by Immunoprecipitation Vero cells grown in T25 flasks were mock-infected, or infected with the defective HSV vectors vIE1GT or vIE1βgal at a MOI of about 1 p.f.u. per cell. After 1 hr of viral adsorption, the inoculum was replaced with fresh DMEM/10% NuSerum. When indicated, tunicamyctn (Sigma, St. Louis Mo.) was added at this time at a final concentration of 10 μg/ml and was maintained during the subsequent labeling of cells.

At 13 hr post infection, the cells in each flask were washed twice with methionine-free DMEM (Irvine Scientific, Santa Ana, Calif.) and labelled with 120 μCi $^{35}$S-methionine (1102 Ci/mmol, 15 mCi/ml; ICN Biomedicals Inc., Costa Mesa, Calif.) in 1.5 ml methionine-free DMEM. The cells were harvested at 16 hr post infection.

Membrane fractions were isolated by differential centrifugation and immunoprecipitated with an anti-GT serum according to the methods of Haspel, et al. (1985). The anti-GT serum used is a rabbit polyclonal serum to a synthetic peptide encoding the 13 amino acids of the C terminus of GT (1:400 dilution; East Acres Biologicals, Southbridge, Mass.). The immunoprecipitated fractions were then run on a 12% SDS-PAGE gel without heating and the proteins were visualized by autoradiography.

FIG. 3 shows the results of vero cells that were mock-infected or infected with the defective vectors, with (lane 2) or without (lanes 1, 3 and 4) the treatment of tunicamycin. In FIG. 3: Lane 1, infected with vIE1βgal; lanes 2 and 3, infected with vIE1GT; lane 4, mock-infected. The sizes of protein standards are shown on the left. Lanes 2 and 3 show immunoprecipitated GT bands at approximately 41 kd and 38 kd, respectively.

EXAMPLE 5

Co-Localization of Glucose Transporter Protein by Double-Indirect Immunofluorescence Co-localization of GT with microtubule-associated protein 2 (MAP2) or glial fibrillary acidic protein (GFAP) antigens was performed on mixed neuronal/glial cultures grown on chamber slides at a density of 2.4×10$^5$ cells/cm$^2$. After 10 days in culture, cells were mock-infected, infected with vIE1GT, or infected with vIE1βgal at a MOI of approximately 0.1 p.f.u. per cell. Approximately, sixteen hours post infection, the cells were fixed with acetone/methanol (3:1), and incubated with normal goat serum (2%;

Vector Laboratories, Inc., Burlingame, Calif.) and human serum (2%; Armour Pharmaceutical Company, Kankakee, Ill.) in phosphate buffered saline (PBS; Maniatis, et al.). The human serum was used to block any Fc receptors potentially induced by viral infection.

GT expression was detected using the anti-GT rabbit serum (1:400 dilution; East Acres Biologicals), followed by a rhodamine-conjugated goat antibody against rabbit IgG (1:80 dilution; Tago, Inc., Burlingame, Calif.). Neurons were identified using a mouse monoclonal antibody against MAP2 (1:100 dilution; Sigma Chemicals) and astrocytes were identified using a mouse monoclonal antibody against GFAP (1:200 dilution; Sigma Chemicals). MAP2 and GFAP immunoreactivities were visualized by a fluorescein-conjugated goat antibody against mouse IgG (1:40 dilution; Tago, Inc.).

FIGS. 4A to 4D show fluorescence microscopy photographs of the above described co-localization studies. FIGS. 4A and 4B show cells double-stained with anti-GT serum (4A) and anti-MAP2 monoclonal antibody (4B). FIGS. 4C and 4D show cells double-stained with anti-GT serum (4C) and anti-GFAP monoclonal antibody (4D). These results indicate that the viral vectors of the present invention are effective to infect both neurons and astrocytes and express protein coding sequences, such as GT sequences, in those cells. Further, the data demonstrate that the glucose transporter protein may be co-localized with microtubule-associated protein and glial fibrillary acidic protein.

EXAMPLE 6

In Vitro [$^{14}$C]-2-Deoxyglucose Uptake

Vero cells and astrocytes were plated in 48-well plates at a density of $1 \times 10^5$ cells per well and mixed neuronal/glial hippocampal cultures were plated at $4 \times 10^5$ cells per well. The cells were mock-infected, infected with vIE1GT or infected with vIE1βgal at a MOI of approximately 1 p.f.u. per cell. Infection was performed at 37° C. or 39° C. as indicated.

Glucose uptake was measured according to a modified method of Horner, et al. (1990). Sixteen to twenty hours after infection, cells in each well were washed twice with phosphate-buffered saline (PBS, 137 mM NaCl/4 mM KCl/8 mM Na$_2$HPO$_4$/1.5 mM K$_2$PO$_4$) warmed to 37° C. and then pulsed with a tracer dose of 0.3 µCi [$^{14}$C]-2-Deoxyglucose (2DG) (55 mCi/mmol, American Radiolabelled Chemicals, Inc., St. Louis, Mo.) in 0.3 ml warm PBS. After 5 minutes, the uptake of glucose was terminated by rinsing the cells twice each with 0.4 mM phloretin (Sigma) in cold PBS (4° C.) and cold PBS. The cells were then lysed in 1% sodium dodecyl sulphate (SDS) in PBS. Radioactivity of the lysate was standardized to protein concentrations as determined by the o-phthaldehyde method (Pierce, Rockford, Ill.) and expressed as the % of mean mock-infected values.

For glucocorticoid studies, corticosterone (Sigma; stock solution of $10^{-2}$M, dissolved in ethanol) was added to the medium (final concentration $10^{-6}$M) after one hour of viral adsorption and maintained throughout the course of the experiment.

Comparisons of glucose uptake rates among various cultures and among various brain regions in vivo (see Example 7) were made by analysis of variance followed by Newman-Keuls post-hoc tests.

A. In Vitro Glucose Uptake.

FIG. 5 presents the results of the above-described 2DG uptake analysis. Uptake of 2DG was significantly higher in vIE1GT-infected cultures versus mock and vIE1βgal-infected cultures ($p<0.001$ for all cases except astroglia, where $p<0.05$; Newman-Keuls post-hoc test following analysis of variance).

B. The In Vitro Effect of vIE1GT Infection and/or Glucocorticoid Treatment on Glucose Transport.

Mixed neuronal/glial cultures from hippocampus were mocked-infected, infected with ts756 or with vIE1GT, with or without the treatment of corticosterone ($10^{-6}$M). Rates of [$^{14}$C]2DG uptake were measured at 16 hr post infection (FIG. 6). As with the experiments described above, vIE1GT infection caused a significant enhancement of glucose uptake in glucocorticoid-free cultures, relative to mock-infected cultures ($p<0.001$, Newman-Keuls test). Glucocorticoid exposure (data shown in FIG. 6) caused a significant decline in glucose uptake in mock-infected cultures ($p<0.001$) but did not alter uptake rates in vIE1GT-infected cultures ($p>0.10$).

EXAMPLE 7

In vivo [$^{14}$C]-2-Deoxyglucose Uptake in Sprague-Dawley Rats

Male Sprague-Dawley rats (375–450 gm; n=6) were catheterized in the femoral vein and artery. Two days later they were microinfused unilaterally in the hippocampus with vIE1GT (2 µl; containing approximately $1 \times 10^5$ p.f.u.) and similar amount of vIE1βgal contralaterally (coordinates with bregma=lambda: AP: 4.1; ML: 2.1; DV: 3.0; Cushman and Pelligrino atlas).

Thirty six to forty eight hours later, [$^{14}$C]2DG in saline (100 µCi/kg body weight) was injected intravenously and 12 timed arterial blood samples were collected to confirm the success of injection. After approximately 45 minutes, rats were overdosed with pentobarbital and decapitated.

Brains were frozen in 2-methylbutanol (–20° C.) and stored at –80° C. 20 µm serial coronal sections were prepared and exposed to X-ray film for 4–5 days. $^{14}$C-standards (Amersham Corporation, Arlington Heights, Ill.) were included with each sheet of film and $^{14}$C levels were quantified in indicated regions using a MCID computerized densitometry and image analysis system (Imaging Research, Inc., Ontario, Canada). For these studies, the kinetic rate constants and the "lumped" constant derived by Sokoloff are applicable (Sokoloff et al., 1977).

FIG. 7 shows a representative coronal section of the hippocampus showing the eight individual regions where glucose uptake was measured. The rectangle in the lower right corner represents the approximate area of measurement in each region.

Figure 8:
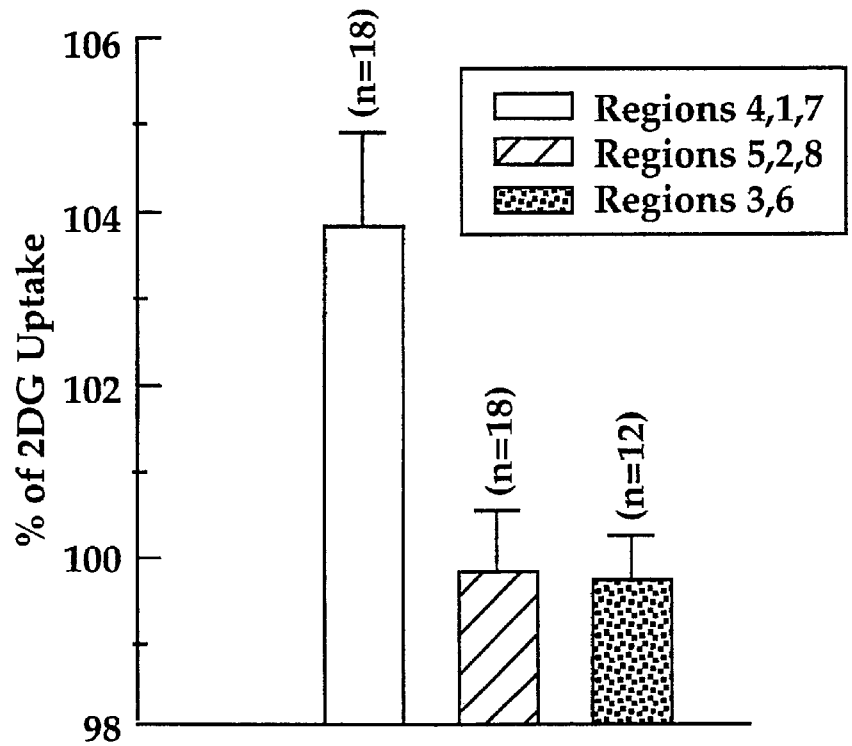
FIG. 8 presents the data of a medial/lateral analysis showing that [$^{14}$C]2DG uptake was enhanced in hippocampal regions nearest to the site of vIE1GT injection.

FIG. 8 presents the results of medial/lateral analysis showing that [$^{14}$C]2DG uptake was enhanced in hippocampal regions nearest to the site of vIE1GT injection. The results in FIG. 8 shows average $^{14}$C levels in each hippocampal region which were determined in 25 sections anterior and posterior to the injection site for the areas shown in FIG. 7. In FIG. 8, uptake in the vIE1GT injected hippocampus is expressed as percentage of uptake in the contralateral vIE1βgal control. In FIG. 8, n=sample size, e.g., for each rat, regions 1, 4 and 7 are grouped and analyzed together. Therefore, for 6 rats, $n=6 \times 3=18$. Same for areas 2, 5 and 8. For areas 3 and 6, $n=6 \times 2=12$); data were pooled for areas 1, 4, and 7; areas 2, 5, and 8; and areas 3 and 6. The results show that uptake was significantly enhanced in vIE1GT-injected sites (relative to vIE1βgal-injected control sites) in areas 1, 4 and 7, but not in other regions ($p<0.01$, Newman-Keuls test following analysis of variance).

FIG. 9 presents the results of anterior/posterior analysis showing that [$^{14}$C]2DG uptake was enhanced nearest to the site of injection of vIE1GT. Four rats were analyzed. Uptake (relative to the contralateral side) is shown in hippocampal region 1 as a function of distance from the injection site in the anterior/posterior plane, with data pooled for every three 20 μm section. Numbers in parenthesis indicate the numbers of sections from the four rats analyzed; numbers varied because, in some cases, sections corresponding to the state distance from the infusion site were not available.

EXAMPLE 8

In situ Hybridization Studies

Two sets of experiments were performed to measure the in vivo expression of microinfused defective virus using in situ hybridization. In the first set, adult male Sprague-Dawley rats (300–350 gm) were microinfused unilaterally in the hippocampus (coordinates with bregma=lambda; AP: 4.1, ML: 2.1; DV: 3.0) with 2 μl vIE1GT (~1×10$^5$ p.f.u.) and similar amounts of vIE1βgal and ts756, or DMEM contralaterally. The animals were sacrificed two days later by decapitation.

In the second set of experiments, adult male Sprague-Dawley rats (250–300 gm) were microinfused unilaterally in Ammon's horn of the hippocampus (AP 4.1, ML 3.0, DV 3.0) with 2 μl of vα4GT (~2×10$^6$ pfu/ml), and similar amounts of vα4βgal and d120, or DMEM contralaterally. The animals were sacrificed 24 hours later by decapitation.

In both sets of experiments, the brains were frozen in 2-methylbutane immediately following decapitation and sectioned on a cryostat (AO Reichert Scientific Instruments, Buffalo, N.Y.). 15 μm thick coronal sections were collected on "VECTABOND" (Vector Laboratories) coated slides and were prepared for hybridization according to the protocol of Sutin, et al. The sections were treated with a hybridization mixture (50% formamide, 4×SSC, 1×Denhardt's solution, 10% dextran sulfate, 250 μg/ml tRNA, 500 μg/ml salmon sperm DNA) containing an oligonucleotide probe end-labelled with $^{35}$S-dATP (approximately 5×10$^5$ c.p.m. per section) for 16 hours at 37° C.

The probe used to detect vIE1GT viral vector-derived GTmRNA from the endogenous version was a 75-mer oligonucleotide antisense to the ie1 promotor (bases −35 to +40). This probe hybridized to the 5' untranslated end of both the GT transcript (from vIE1GT) and the lacZ transcript (from vIE1βgal).

The probe used to detect vα4GT viral vector-derived GT mRNA was a 26 bp oligonucleotide antisense to the 5' untranslated region (bases +1 to +26) of the α4 transcript. A sense oligo was used as control probe.

Following hybridization, the sections were washed (Sutin, et al.), coated with emulsion, exposed for 15 days at 4° C., developed and stained with 0.1% thionin.

Figure 10A:
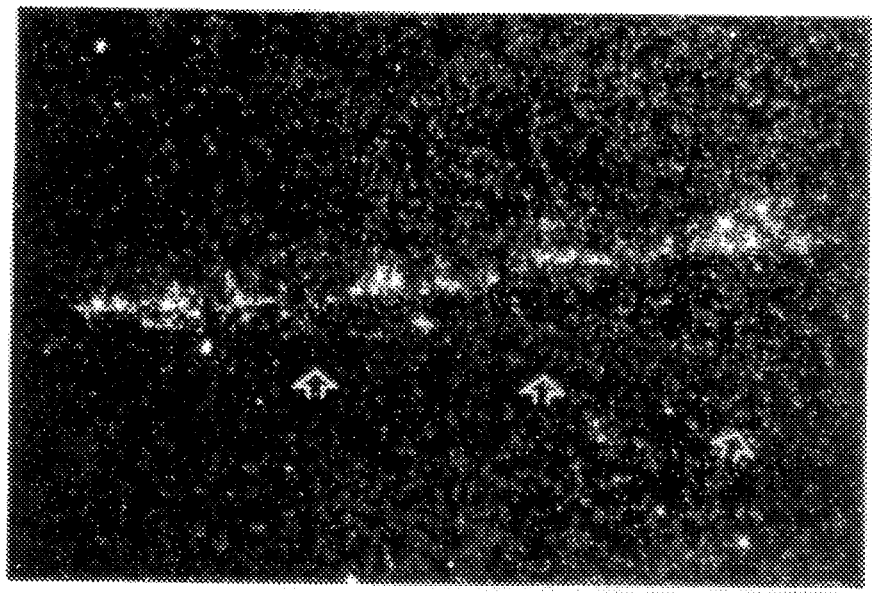
FIGS. 10A, 10B and 10C show patterns of gene expression in hippocampus from vIE1GT (FIG. 10A), vIE1βgal (FIG. 10B) and vα4GT (FIG. 10C) vectors as detected by in situ hybridization.
Figure 10B:
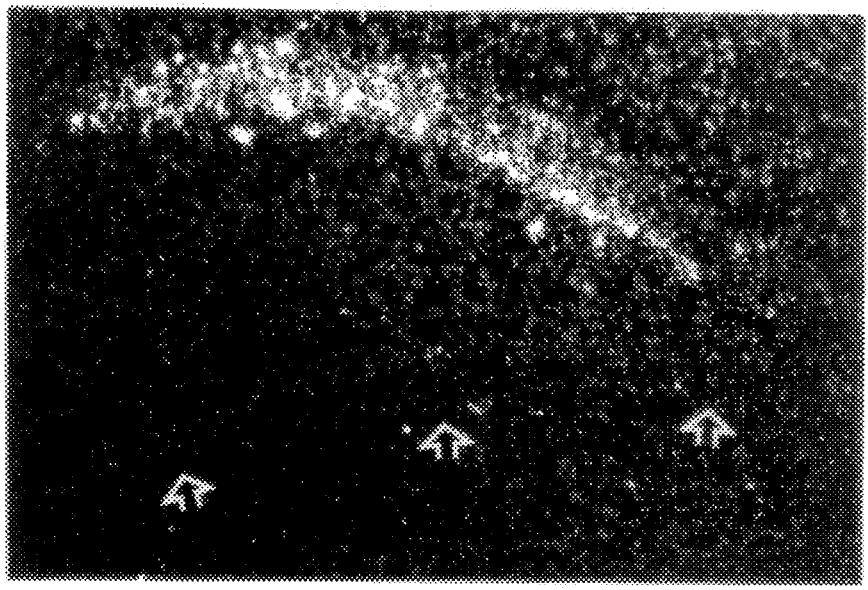
Figure 10C:
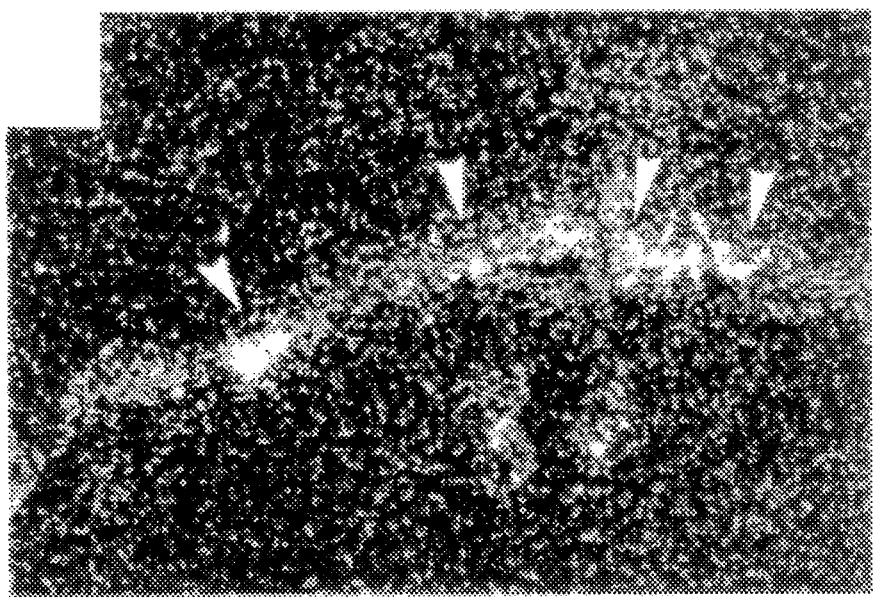

FIG. 10 shows the results of gene expression from vIE1GT, vIE1βgal and vα4GT in hippocampus as detected by in situ hybridization. FIGS. 10A, 10B and 10C illustrate dark field microscopy photographs that demonstrate positive hybridization signals on the dorsal blade of the dentate gyrus from vIE1GT-(FIG. 10A), vIE1βgal-(FIG. 10B) and vα4GT-(FIG. 10C) infected animals. The ventral blade of the dentate gyrus is outlined with arrow heads in FIGS. 10A and 10B. The hybridization signal, on the dorsal horn of the dentate, is identified by arrowheads in FIG. 10C.

With regard to the second set of experiments, performed with vα4GT and illustrated in FIG. 10C, contralateral cell fields receiving a matching titer of d120 did not produce any detectable signals, indicating that the unstable truncated ICP4 transcript from d120 did not account for the positive signal (DeLuca, et al., 1985).

EXAMPLE 9

Metabolism and Survival of Hypoglycemic Neuronal/Glial Cultures

Neuronal/glial cultures exposed to hypoglycemic conditions typically exhibit a substantial decrease in metabolism followed by cell death of the neurons (Seisjo). Experiments were performed to determine if infection by GT-expressing virus was effective to inhibit the decrease in metabolism and cell death following exposure to hypoglycemic conditions.

A. Metabolism.

Mixed neuronal/glial cultures (50:50; 8×10$^5$ cells plated in 1 cm transwells (Molecular Devices Corp., Menlo Park, Calif.)) were prepared from the hippocampi of day 18 fetal Sprague-Dawley rats as described in Example 1. On day 5, cultures were either mock-infected, infected with vIE1GT or infected with vIE1βgal at a MOI of about 0.2 p.f.u. per cell for IE1 virus and 1.8 p.f.u. for helper virus). Twenty hours after infection the cultures were placed in a cytosensor microphysiometer (Molecular Devices, Menlo Park, Calif.), which quantifies cellular metabolism by measuring the extracellular acidification rate in units of mVolts/sec (McConnell, 1992; Raley-Susman, et al., 1992).

Baseline metabolic rate measurements were made in high glucose medium (20 mM glucose in unbuffered Dulbecco's modified Eagle's medium (DMEM)) over 1 hour. The metabolic rate under "hypoglycemic conditions" was measured in low glucose medium (0.2 mM glucose in unbuffered DMEM) over 1 hour.

Ten-second measurements were taken at 1 minute intervals and averaged to obtain data points every five minutes. The 5 minute data points were further averaged within treatment groups of cultures (one culture per transwell). The mean metabolic rates of vIE1GT (n=10 wells), vIE1βgal (n=12 wells) and mock infected (n=9 wells) cultures during the 30 minute hypoglycemic period are reported as a percent of baseline measures ±SEM in FIG. 11. All groups were significantly different from each other (p<0.0001, Fisher Least Significant Difference Procedure).

Both vIE1GT and vIE1βgal exhibited elevated baseline metabolic rates relative to mock infected cultures (112.6±6.6 and 110.8±5.6 mVolts/sec, respectively, versus 81.8±3.3 mVolts/sec), a characteristic also observed in cultures infected with helper virus alone (115.9±5.2 mVolts/sec). This indicates that the elevation arose from infection with HSV virions and not the overexpression of GT or lacZ genes.

Because only approximately 10–15% of the cells in any give culture were infected by vectors (as determined by X-gal staining of vIE1βgal-infected cultures and calculation from input MOI), the percentage increase in metabolism per vIE1GT infected cell was 7–10× greater than that observed per culture well (~10%), yielding an actual metabolic increase of approximately 70–100% per cell. Of the infected cells 90% were neuronal, suggesting that the observed effects of vIE1GT infection arose from enhanced neuronal, and not glial, glucose uptake.

B. Survival.

Mixed neuronal/glial hippocampal cultures (Example 1) were grown in 48-well plates in MEM-PAK medium supplemented with 10% horse serum and 30 mM glucose. Four days after plating, the cultures were treated with cytosine arabinofuranoside to retard astrocyte growth.

At day 10 to 12 cells were infected with vIE1GT or vIE1βgal at a MOI of 0.2 p.f.u. per cell. Sixteen hours later, media were removed and replaced with DMEM containing 5 mM, 1 mM or 0.5 mM glucose. The cells were further incubated for 8 hrs, then fixed with methanol and stained for MAP2 immunoreactivity as described above. Surviving neurons (positive-staining cells with intact processes) were counted.

The data are summarized in FIG. 12. The number of surviving neurons in infected cultures was expressed as the percent of neurons in uninfected control cultures (i.e. cultures that had not been subjected to glucose manipulation). The percent of surviving neurons decreases with decreasing glucose in all samples, but infection with a GT-expressing vector results in more neurons surviving at any given glucose concentration that survive in control cultures. Significant differences were observed between vIE1GT and vIE1βgal infected cultures at all three glucose concentrations ($p<0.01$ by ANOVA).

EXAMPLE 10

Co-localization of GT and β-gal in infected VERO cells

Co-localization of GT and β-gal was performed on Vero cells grown to 70% confluency in DMEM with 10% NuSerum (Collaborative Research, Inc., Bedford, Mass.) on glass coverslips. The cells were infected with vα22βgalα4GT or with vα4GT at a MOI of approximately 0.1 p.f.u. per cell.

The lacZ gene under the α4 and ie1 promoters reached maximal expression in infected vero cultures within 8 and 12 hrs, respectively. Accordingly, approximately 12 hours post infection, the cells were fixed with acetone/methanol (3:1) and incubated with normal goat serum (15%; Vector Laboratories, Burlingame, Calif.) and human immune globulin (15%; Armour Pharmaceutical Co., Kankakee, Ill.) in PBS to block any Fc receptors potentially induced by viral infection. The cells were then labeled by sequential 45 minute incubations, at 20° C., with anti-β-galactosidase rabbit serum (1:100 dilution; Cappel, Durham, N.C.), biotinylated goat antibody against rabbit IgG (1:100; Vector Laboratories), and avidin-rhodamine (1:250; Vector Laboratories). The cells were further incubated with anti-GT rabbit serum (1:100; East Acres Biologicals, Southbridge, Mass.), biotinylated goat antibody against rabbit IgG (1:100, Vector Laboratories), and avidin-fluorescein (1:100; Vector). The cells were washed with PBS three times, three minutes per wash, between each incubation step.

Figure 13A:
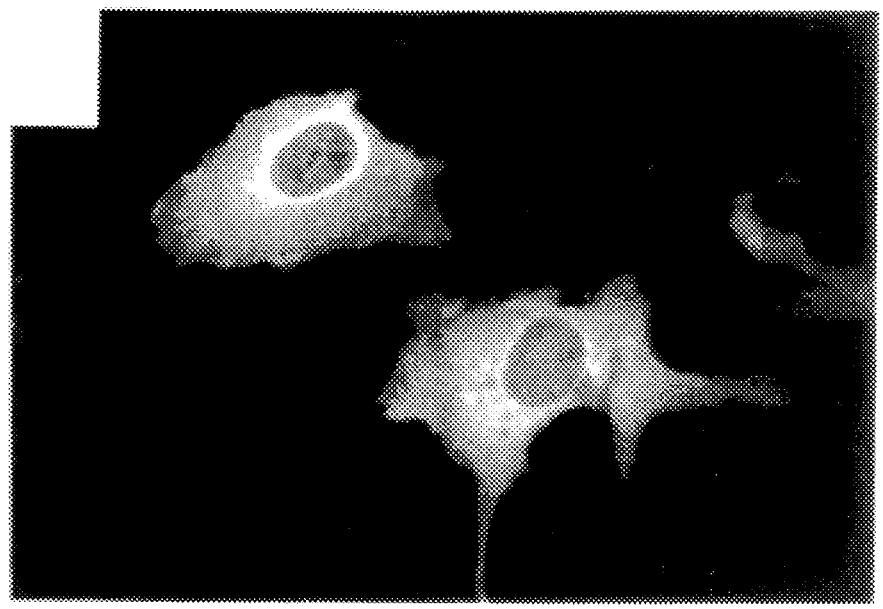
FIGS. 13A and 13B show double indirect immunofluorescence micrographs of vα22βgalα4GT-infected Vero cells stained for GT (FIG. 13A) and β-gal (FIG. 13B).
Figure 13B:
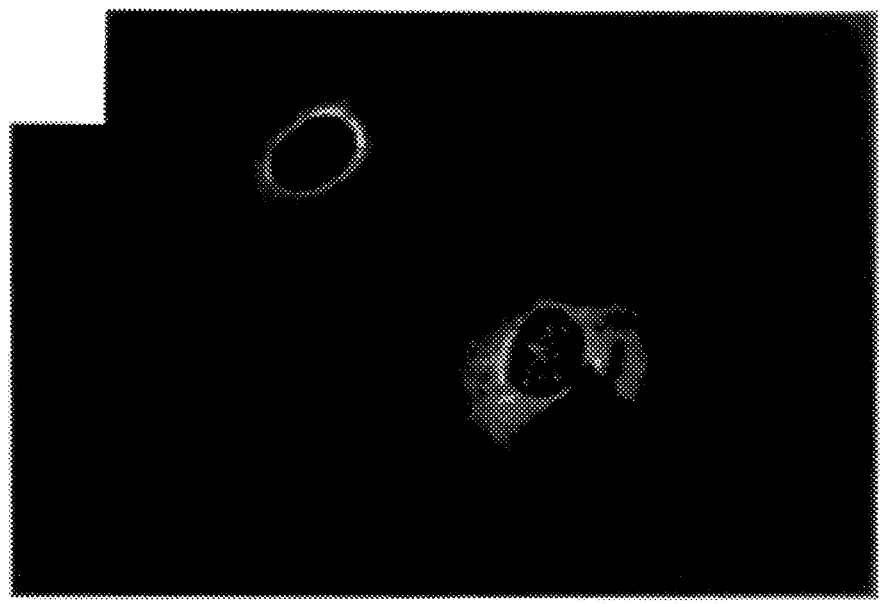
Figure 14A:
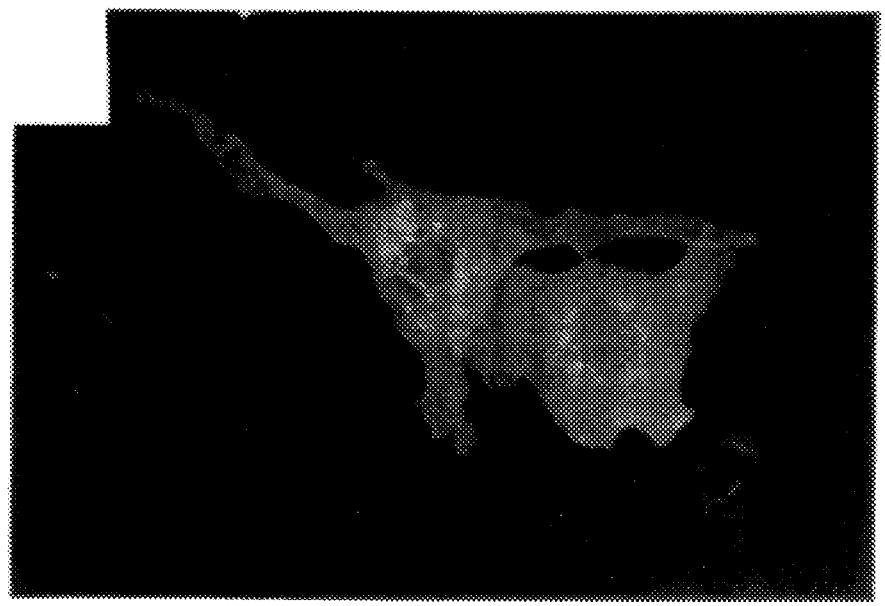
FIGS. 14A and 14B show double indirect immunofluorescence micrographs of vα4GT-infected Vero cells stained for GT (FIG. 14A) and β-gal (FIG. 14B).
Figure 14B:
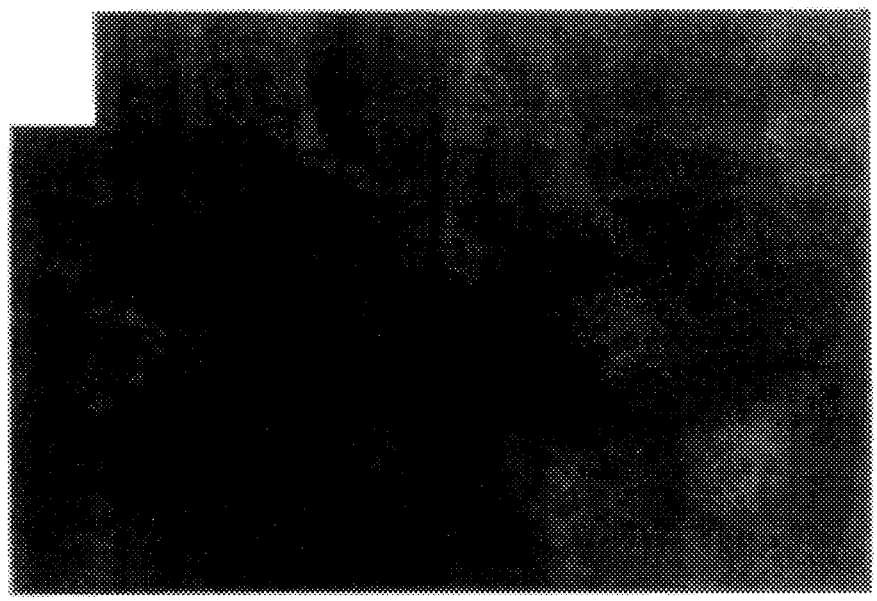

Exemplary fluorescence microscope images are shown in FIGS. 13A, 13B, 14A and 14B. FIGS. 13A and 13B illustrate colocalization of GT (FIG. 13A) and β-gal (FIG. 13B) in cells infected with vα22βgalα4GT. Double immunofluorescence of vα4GT-infected Vero cells shows a strong GT signal (FIG. 14A) but no β-gal signal (FIG. 14B).

EXAMPLE 11

Expression of β-gal in Infected Cells in vivo

Hippocampi of adult male Sprague-Dawley rats were microinfused with either vIE1GT or vα22βgalα4GT as described above (vIE1GT as in the first set of experiments described in Example 8 and vα22βgalα4GT as in the second set), sacrificed and brains were frozen and sectioned as in Example 8.

The sections were mounted on gelatin substrated slides and stained for X-gal (0.5 mg/ml X-gal in 5% DMSO, 25 mM KFeCN in PBS, 20° C.; Ho, et al., 1988) or X-gal with cresyl violet counterstain. In the latter procedure, the sections were stained in X-gal for six hours, dehydrated with ethanol/xylene, rehydrated, stained with eosin or cresyl violet, dehydrated again and mounted (Sapolsky, 1986).

An exemplary bright-field microscope image of a section containing vIE1GT-infected cells stained for X-gal is shown in FIG. 15. β-gal-expressing cells are visualized as darkly-stained cells on the dorsal blade of the dentate gyrus. Exemplary images of sections from the dentate containing vα22βgalα4GT-infected cells stained with X-gal and cresyl violet are shown in FIGS. 16A (at 20× magnification) and 16B (at 40× magnification).

Microinfusion of $4 \times 10^3$ vα4βgal virions resulted in the infection of 725±44 neurons, as assessed by counting labeled neurons in X-gal/eosin stained 25 mm hippocampal sections (n=20 brains). This indicates that approximately 18% of infused virions successfully infected neurons. Most labeling was confined within the dentate (about 800 mm anterior and posterior to the cannula tract) and to a limited number of neurons in the CA3 region (about 200 mm medial, lateral, anterior and posterior to the cannula tract).

EXAMPLE 12

In-vivo Neuronal Protection Against KA Lesions by Infection with a Vector Encoding GT A. Neuroprotection by Infection with vα4GT.

Male Sprague-Dawley rats were microinfused unilaterally in the hippocampus (coordinates AP 4.1, ML 3.0, DV 3.0) with either 2 μl of vα4GT and d120, or 2 μl of vα4βgal and d120 (viral vector titer of $\sim 1 \times 10^7$ p.f.u./ml, helper virus titer of $\sim 1-5 \times 10^7$ p.f.u./ml). The contralateral cell field received 2 μl of virus-free DMEM. All microinfusions were made through stereotaxically-implanted cannulae, which allowed the delivery of vector and kainic acid (KA) to the same site. Vector was delivered either 12 hours before, simultaneously with, 1 hour after, or 4 hours after bilateral delivery of KA (0.035 mg in 1 ml phosphate buffered saline).

Animals receiving the vector 12 hours before KA infusion were broken into hypo-, normo- and hyperglycemic groups. Normo-glycemic rats were unmanipulated, while hypoglycemic animals were deprived of food for 24 hours prior to KA delivery. Hyperglycemic rats were given 20% glucose drinking water for 12 hours before and after KA infusion, and were injected with glucose (6 g/kg body weight (b.w.) in 5 ml saline intraperitonally (I.P.)) at the time of the KA infusion. These altered dietary regimes depressed or elevated circulating glucose concentrations by 30% relative to normal levels (Sapolsky and Stein, 1989).

Animals were sacrificed 48 hours after KA administration, perfused with 2% paraformaldehyde and brains were removed and post-fixed (2% paraformaldehyde, 20% sucrose) for 2 days before sectioning. 25 mm coronal sections were collected every 100 mm for 800–1000 mm anterior and posterior to the infusion site. Sections were stained with cresyl-violet as in Example 11 above. Damage was quantified by measuring the length of the deletions in the CA3 cell fields with a calibrated ocular grid at 40× magnification.

FIGS. 17A and 17B show representative damage in CA3 hippocampal cell fields of a hypoglycemic rat that had received KA only (FIG. 17A) or KA with vα4GT. The lesion following KA infusion without viral vector (arrowheads, FIG. 17A) measured 0.91 mm, whereas the lesion following KA infusion with simultaneous delivery of vα4GT (arrowheads, FIG. 17B) measured 0.54 mm. The data suggest that the extent of KA-induced damage is reduced by the simultaneous delivery of vα4GT. The dentate (DG), CA 3, needle tract (NT) and lesion (arrows) are indicated.

Measurements in successive sections were integrated to arrive at a total volume of damage which was expressed as the percent reduction in damage relative to the contralateral control cell field for each brain. Damage measured by this method correlates with cell counting techniques (Stein et al.).

The reduced data, shown in FIG. 18, are presented as the mean within each group ±SEM. Sample sizes (number of brains assessed for damage) are given beneath each bar. Hypoglycemic rats microinfused with vα4GT showed a significant reduction in the percent damage in CA3 relative to the contralateral control cell field ($p<0.05$, paired t-test). Normo-glycemic animals also showed a significant but smaller reduction ($p<0.05$).

Figure 19:
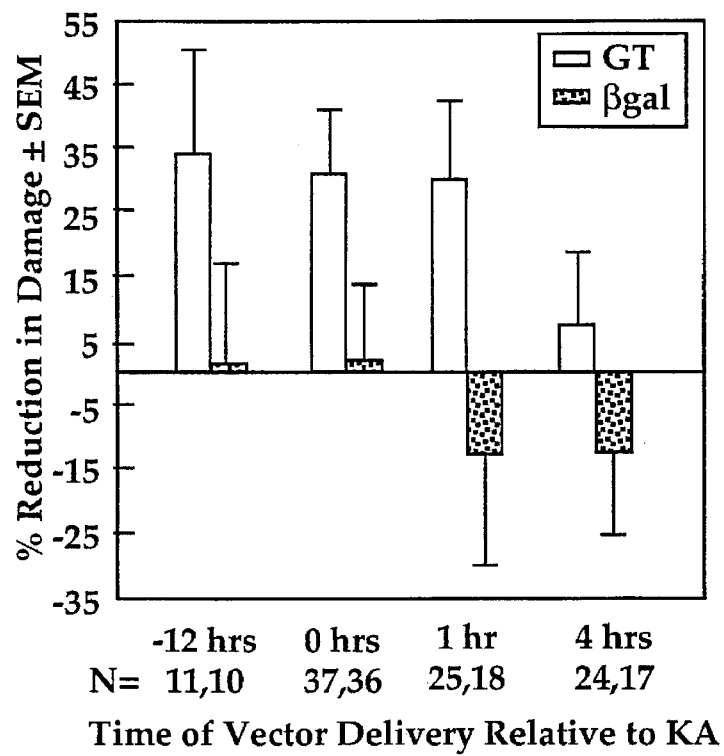
FIG. 19 shows the percent reduction in KA-induced damage in hypo-glycemic rats by infection with vα4GT or vα4βgal 12 hours before, simultaneously with, one hour after or four hours after KA infusion.

FIG. 19 shows the effects of the time between vector administration and KA infusion in hypoglycemic rats. Animals receiving vector prior to, simultaneously with, or one hour after KA showed significant CA3 protection ($p<0.05$). Infusion of vα4GT four hours after KA did not result in significant protection. Infusion of vα4βgal was ineffective at reducing neural damage regardless of the time at which it was administered.

B. Correlation of β-gal Expression with Neuroprotection.

Animals were bilaterally microinfused in the hippocampus with the vector vα22βgalα4GT (2 μl; $1\times10^4$ to $1\times10^7$ p.f.u./ml; coordinates AP 4.1, ML 3.0, DV 3.0 and AP 4.1, ML 2.0, DV 3.0) and with KA (0.035 mg; coordinates AP 4.1, ML 3.0, DV 3.0). The animals were sacrificed and brain sections prepared and stained for X-gal with cresyl-violet counterstain as described in part A, above. For each hemisphere of each brain, total CA3 damage was determined and plotted against the number of β-gal-positive dentate neurons counted in corresponding sections. The data are fitted with a straight line ($y=5.6-6.7*10^{-3}x$; $r^2=0.561$; $n=44$).

While the invention has been described with reference to specific methods and embodiments, it will be appreciated that various modifications and changes may be made without departing from the invention.

It is claimed:

1. An amplicon comprising
   herpes simplex virus (HSV) sequences containing an HSV origin of DNA replication and HSV cleavage/packaging signals,
   glucose transporter protein coding sequences, where the coding sequences are flanked by regulatory elements effective to allow expression of the coding sequences in a eucaryotic host, and
   bacterial plasmid sequences that allow the amplicon to be amplified in prokaryotic cells.

2. The amplicon of claim 1, where the HSV sequences are derived from Herpes Simplex Virus I (HSV-1).

3. The amplicon of claim 1, where the glucose transporter protein coding sequences are obtained from rat or human coding sequences.

4. The amplicon of claim 1, where said regulatory elements include promoter, translation start, and polyadenylation signals.

5. The amplicon of claim 4, wherein said promoter is selected from the group consisting of the human cytomegalovirus ie1 promoter, the HSV-1 ICP4 (α4) promoter and the HSV-1 α22 promoter.

6. An expression vector, comprising
   a defective herpes virus into which at least one copy of an amplicon has integrated, where the amplicon contains (i) herpes simplex virus (HSV) sequences containing an HSV origin of DNA replication and HSV cleavage/packaging signals, (ii) glucose transporter protein coding sequences, where the coding sequences are flanked by regulatory elements effective to allow expression of the coding sequences in a eucaryotic host, and (iii) bacterial plasmid sequences that allow the amplicon to be amplified in prokaryotic cells.

7. The expression vector of claim 6, where in the amplicon the HSV sequences are derived from Herpes Simplex Virus I.

8. The expression vector of claim 6, where in the amplicon the glucose transporter protein coding sequences are obtained from rat or human coding sequences.

9. A method of making a defective virus expression vector, comprising,
   generating an amplicon that contains (i) herpes simplex virus (HSV) sequences containing an HSV origin of DNA replication and HSV cleavage/packaging signals, (ii) glucose transporter protein coding sequences, where the coding sequences are flanked by regulatory elements effective to allow expression of the coding sequences in a eucaryotic host, and (iii) bacterial plasmid sequences that allow the vector to be amplified in prokaryotic cells,
   co-transfecting into permissive eucaryotic cells said amplicon with a helper virus, where the helper virus is a conditionally replication-defective herpes simplex virus,
   passaging the eucaryotic cells,
   releasing the defective virus from the cells.

10. The method of claim 9, where said conditionally replication-defective herpes simplex virus carries a temperature-sensitive replication defective mutation.

11. The method of claim 9, where said conditionally replication-defective herpes simplex virus carries a deletion in a gene required for replication.

12. The method of claim 11, wherein said permissive eucaryotic cell carries a functional copy of the gene required for replication.

* * * * *

UNITED STATES PATENT AND TRADEMARK OFFICE
CERTIFICATE OF CORRECTION

PATENT NO. : 5,661,033

DATED : August 26, 1997

INVENTOR(S) : Dora Yuk-Wai Ho; Robert Morris Sapolsky; Edward S. Mocarski, Jr.

It is certified that error appears in the above-indentified patent and that said Letters Patent is hereby corrected as shown below:

column 1, line 8 thereof, please insert:

--This work was supported in part by the National Science Foundation Grant BNS8657742. Accordingly, the United States Government has certain rights in this invention.--

Signed and Sealed this

Fourteenth Day of July, 1998

Attest:

BRUCE LEHMAN

Attesting Officer

Commissioner of Patents and Trademarks